(12) United States Patent
Ayer et al.

(10) Patent No.: US 11,788,073 B2
(45) Date of Patent: *Oct. 17, 2023

(54) POLYMERASE VARIANTS AND USES THEREOF

(71) Applicant: Roche Sequencing Solutions, Inc., Pleasanton, CA (US)

(72) Inventors: Aruna Ayer, Santa Clara, CA (US); Cleoma Arnold, San Jose, CA (US); Charles Wayan Schwab, San Ramon, CA (US); Eileen Thai, San Jose, CA (US); Ilya Lederman, San Francisco, CA (US); Colin Alexander McGaw, Santa Clara, CA (US); Tyler O'Brien Shultz, Santa Clara, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 69 days.

This patent is subject to a terminal disclaimer.

(21) Appl. No.: 17/249,605

(22) Filed: Mar. 5, 2021

(65) Prior Publication Data
US 2021/0189355 A1     Jun. 24, 2021

Related U.S. Application Data

(63) Continuation of application No. 16/694,985, filed on Nov. 25, 2019, now Pat. No. 10,968,438, which is a continuation of application No. 15/151,364, filed on May 10, 2016, now Pat. No. 10,526,588, which is a continuation-in-part of application No. 15/012,317, filed on Feb. 1, 2016, now Pat. No. 10,308,918.

(60) Provisional application No. 62/202,895, filed on Aug. 9, 2015, provisional application No. 62/161,571, filed on May 14, 2015.

(51) Int. Cl.
*C12N 9/12*     (2006.01)

(52) U.S. Cl.
CPC ......... *C12N 9/1241* (2013.01); *C12N 9/1252* (2013.01); *C12Y 207/07* (2013.01); *C12Y 207/07007* (2013.01)

(58) Field of Classification Search
CPC .... C12N 9/12; C12N 9/1252; C07K 2319/21; C12Y 207/07007
See application file for complete search history.

(56) References Cited

U.S. PATENT DOCUMENTS

| 10,526,588 | B2 * | 1/2020 | Ayer | ............ C12N 9/1241 |
| 2020/0190489 | A1 * | 6/2020 | Ayer | ............ C12N 9/1252 |

* cited by examiner

*Primary Examiner* — Maryam Monshipouri
(74) *Attorney, Agent, or Firm* — Pamela C. Ancona; Bryan Jones

(57) ABSTRACT

Described herein is a variant pol6 polymerase having at least one mutation selected from H223, N224, Y225, H227, I295, Y342, T343, I357, S360, L361, I363, S365, S366, Y367, P368, D417, E475, Y476, F478, K518, H527, T529, M531, N535, G539, P542, N545, Q546, A547, L549, I550, N552, G553, F558, A596, G603, A610, V615, Y622, C623, D624, I628, Y629, R632, N635, M641, A643, I644, T647, I648, T651, I652, K655, W656, D657, V658, H660, F662, L690 and combinations thereof.

5 Claims, 9 Drawing Sheets
Specification includes a Sequence Listing.

kchem Assay

REACTION CAN BE EXECUTED USING STOPPED-FLOW OR PLATE-READER

SYRINGE A:
- POLYMERASE
- FLUORESCEIN-LABELED TEMPLATE/PRIMER
- 75mM KCl, HEPES pH 7.5

SYRINGE B:
- MgCl
- dAnP-Cy3 (QUENCHER)
- 75mM KCl, pH 7.5

WHEN MIXED OR INJECTED:
— POLYMERASE FORMS TERNARY COMPLEX, Cy3 QUENCHES FLUORESCEIN
— POLYMERASE INCORPORATES NUCLEOTIDE RELEASING CLEAVAGE PRODUCT, POLYPHOSPHATE WITH ATTACHED QUENCHER (nP-Cy3) RELEASING SIMULTANEOUSLY QUENCH

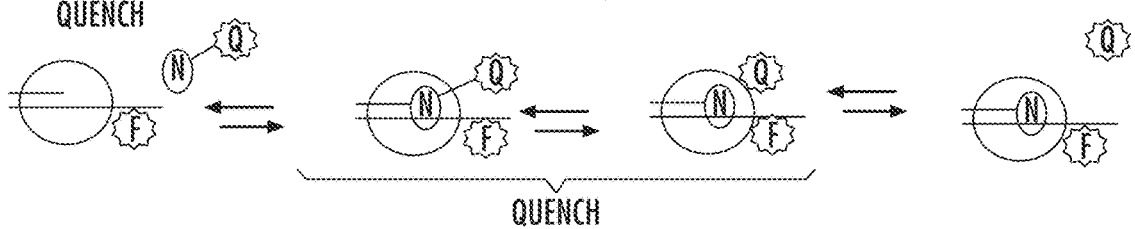

FIG. 2 koff Assay

REACTION CAN BE EXECUTED USING STOPPED-FLOW OR PLATE-READER

SYRINGE A: (PRE-INCUBATE ~10min)
- POLYMERASE
- FLUORESCEIN-LABELED TEMPLATE/PRIMER
- 75mM KCl, 25 HEPES pH 7.5
- CaCl2
- dNnP-Cy3 (QUENCHER)

SYRINGE B:
- CaCl2
- dNTP (IN EXCESS)
- 75mM KCl, 25mM HEPES pH 7.5

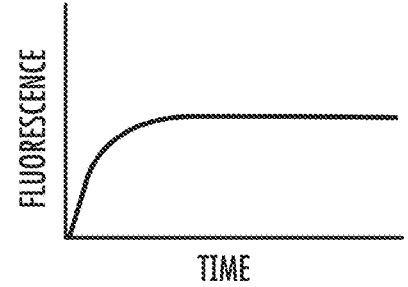

PREINCUBATION:
— ADD dNnP-Cy3, POLYMERASE FORMS TERNARY COMPLEX (QUENCHED). CAN'T INCORPORATE

WHEN MIXED:
— dATP CHASE: dNTP COMPETES WITH dNnP-Cy3 FOR ASSOCIATION (INCR FLUORESCENE)

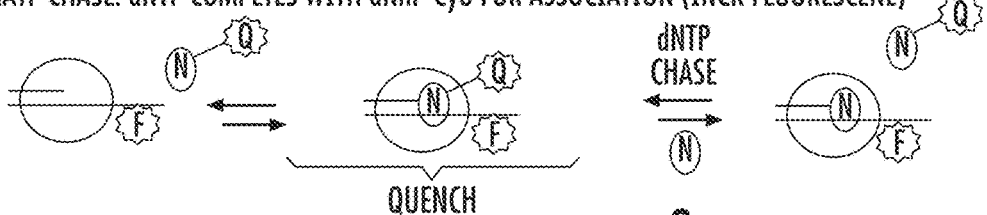

FIG. 3

SEQUENCE LISTING

```
<160> NUMBER OF SEQ ID NOS: 9

<210> SEQ ID NO 1
<211> LENGTH: 727
<212> TYPE: PRT
<213> ORGANISM: Clostridium phage phiCPV4

<400> SEQUENCE: 1

Met Asp Lys His Thr Gln Tyr Val Lys Glu His Ser Phe Asn Tyr Asp
1               5                   10                  15

Glu Tyr Lys Lys Ala Asn Phe Asp Lys Ile Glu Cys Leu Ile Phe Asp
            20                  25                  30

Thr Glu Ser Cys Thr Asn Tyr Glu Asn Asp Asn Thr Gly Ala Arg Val
        35                  40                  45

Tyr Gly Trp Gly Leu Gly Val Thr Arg Asn His Asn Met Ile Tyr Gly
    50                  55                  60

Gln Asn Leu Asn Gln Phe Trp Glu Val Cys Gln Asn Ile Phe Asn Asp
65                  70                  75                  80

Trp Tyr His Asp Asn Lys His Thr Ile Lys Ile Thr Lys Thr Lys Lys
                85                  90                  95

Gly Phe Pro Lys Arg Lys Tyr Ile Lys Phe Pro Ile Ala Val His Asn
            100                 105                 110

Leu Gly Trp Asp Val Glu Phe Leu Lys Tyr Ser Leu Val Glu Asn Gly
        115                 120                 125

Phe Asn Tyr Asp Lys Gly Leu Leu Lys Thr Val Phe Ser Lys Gly Ala
    130                 135                 140

Pro Tyr Gln Thr Val Thr Asp Val Glu Glu Pro Lys Thr Phe His Ile
145                 150                 155                 160

Val Gln Asn Asn Asn Ile Val Tyr Gly Cys Asn Val Tyr Met Asp Lys
                165                 170                 175

Phe Phe Glu Val Glu Asn Lys Asp Gly Ser Thr Thr Glu Ile Gly Leu
            180                 185                 190
```

-continued

```
Cys Leu Asp Phe Phe Asp Ser Tyr Lys Ile Ile Thr Cys Ala Glu Ser
            195                 200                 205
Gln Phe His Asn Tyr Val His Asp Val Asp Pro Met Phe Tyr Lys Met
        210                 215                 220
Gly Glu Glu Tyr Asp Tyr Asp Thr Trp Arg Ser Pro Thr His Lys Gln
225                 230                 235                 240
Thr Thr Leu Glu Leu Arg Tyr Gln Tyr Asn Asp Ile Tyr Met Leu Arg
                245                 250                 255
Glu Val Ile Glu Gln Phe Tyr Ile Asp Gly Leu Cys Gly Gly Glu Leu
            260                 265                 270
Pro Leu Thr Gly Met Arg Thr Ala Ser Ser Ile Ala Phe Asn Val Leu
        275                 280                 285
Lys Lys Met Thr Phe Gly Glu Glu Lys Thr Glu Glu Gly Tyr Ile Asn
    290                 295                 300
Tyr Phe Glu Leu Asp Lys Lys Thr Lys Phe Glu Phe Leu Arg Lys Arg
305                 310                 315                 320
Ile Glu Met Glu Ser Tyr Thr Gly Gly Tyr Thr His Ala Asn His Lys
                325                 330                 335
Ala Val Gly Lys Thr Ile Asn Lys Ile Gly Cys Ser Leu Asp Ile Asn
            340                 345                 350
Ser Ser Tyr Pro Ser Gln Met Ala Tyr Lys Val Phe Pro Tyr Gly Lys
        355                 360                 365
Pro Val Arg Lys Thr Trp Gly Arg Lys Pro Lys Thr Glu Lys Asn Glu
    370                 375                 380
Val Tyr Leu Ile Glu Val Gly Phe Asp Phe Val Glu Pro Lys His Glu
385                 390                 395                 400
Glu Tyr Ala Leu Asp Ile Phe Lys Ile Gly Ala Val Asn Ser Lys Ala
                405                 410                 415
Leu Ser Pro Ile Thr Gly Ala Val Ser Gly Gln Glu Tyr Phe Cys Thr
            420                 425                 430
Asn Ile Lys Asp Gly Lys Ala Ile Pro Val Tyr Lys Glu Leu Lys Asp
        435                 440                 445
Thr Lys Leu Thr Thr Asn Tyr Asn Val Val Leu Thr Ser Val Glu Tyr
    450                 455                 460
Glu Phe Trp Ile Lys His Phe Asn Phe Gly Val Phe Lys Lys Asp Glu
465                 470                 475                 480
Tyr Asp Cys Phe Glu Val Asp Asn Leu Glu Phe Thr Gly Leu Lys Ile
                485                 490                 495
Gly Ser Ile Leu Tyr Tyr Lys Ala Glu Lys Gly Lys Phe Lys Pro Tyr
            500                 505                 510
Val Asp His Phe Thr Lys Met Lys Val Glu Asn Lys Lys Leu Gly Asn
        515                 520                 525
Lys Pro Leu Thr Asn Gln Ala Lys Leu Ile Leu Asn Gly Ala Tyr Gly
    530                 535                 540
Lys Phe Gly Thr Lys Gln Asn Lys Glu Glu Lys Asp Leu Ile Met Asp
545                 550                 555                 560
Lys Asn Gly Leu Leu Thr Phe Thr Gly Ser Val Thr Tyr Glu Gly
                565                 570                 575
Lys Glu Phe Tyr Arg Pro Tyr Ala Ser Phe Val Thr Ala Tyr Gly Arg
            580                 585                 590
Leu Gln Leu Trp Asn Ala Ile Ile Tyr Ala Val Gly Val Glu Asn Phe
        595                 600                 605
```

```
Leu Tyr Cys Asp Thr Asp Ser Ile Tyr Cys Asn Arg Glu Val Asn Ser
    610                 615                 620

Leu Ile Glu Asp Met Asn Ala Ile Gly Glu Thr Ile Asp Lys Thr Ile
625                 630                 635                 640

Leu Gly Lys Trp Asp Val Glu His Val Phe Asp Lys Phe Lys Val Leu
            645                 650                 655

Gly Gln Lys Lys Tyr Met Tyr His Asp Cys Lys Glu Asp Lys Thr Asp
            660                 665                 670

Leu Lys Cys Cys Gly Leu Pro Ser Asp Ala Arg Lys Ile Ile Ile Gly
            675                 680                 685

Gln Gly Phe Asp Glu Phe Tyr Leu Gly Lys Asn Val Glu Gly Lys Lys
            690                 695                 700

Gln Arg Lys Lys Val Ile Gly Gly Cys Leu Leu Leu Asp Thr Leu Phe
705                 710                 715                 720

Thr Ile Lys Lys Ile Met Phe
                725

<210> SEQ ID NO 2
<211> LENGTH: 739
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met His His His His His His His Ser Gly Gly Ser Asp Lys His
1               5                   10                  15

Thr Gln Tyr Val Lys Glu His Ser Phe Asn Tyr Asp Glu Tyr Lys Lys
            20                  25                  30

Ala Asn Phe Asp Lys Ile Glu Cys Leu Ile Phe Asp Thr Glu Ser Cys
        35                  40                  45

Thr Asn Tyr Glu Asn Asp Asn Thr Gly Ala Arg Val Tyr Gly Trp Gly
    50                  55                  60

Leu Gly Val Thr Arg Asn His Asn Met Ile Tyr Gly Gln Asn Leu Asn
65                  70                  75                  80

Gln Phe Trp Glu Val Cys Gln Asn Ile Phe Asn Asp Trp Tyr His Asp
                85                  90                  95

Asn Lys His Thr Ile Lys Ile Thr Lys Thr Lys Gly Phe Pro Lys
            100                 105                 110

Arg Lys Tyr Ile Lys Phe Pro Ile Ala Val His Asn Leu Gly Trp Asp
            115                 120                 125

Val Glu Phe Leu Lys Tyr Ser Leu Val Glu Asn Gly Phe Asn Tyr Asp
            130                 135                 140

Lys Gly Leu Leu Lys Thr Val Phe Ser Lys Gly Ala Pro Tyr Gln Thr
145                 150                 155                 160

Val Thr Asp Val Glu Glu Pro Lys Thr Phe His Ile Val Gln Asn Asn
                165                 170                 175

Asn Ile Val Tyr Gly Cys Asn Val Tyr Met Asp Lys Phe Phe Glu Val
            180                 185                 190

Glu Asn Lys Asp Gly Ser Thr Thr Glu Ile Gly Leu Cys Leu Asp Phe
        195                 200                 205

Phe Asp Ser Tyr Lys Ile Ile Thr Cys Ala Glu Ser Gln Phe His Asn
    210                 215                 220
```

```
Tyr Val His Asp Val Asp Pro Met Phe Tyr Lys Met Gly Glu Glu Tyr
225                 230                 235                 240

Asp Tyr Asp Thr Trp Arg Ser Pro Thr His Lys Gln Thr Thr Leu Glu
            245                 250                 255

Leu Arg Tyr Gln Tyr Asn Asp Ile Tyr Met Leu Arg Glu Val Ile Glu
        260                 265                 270

Gln Phe Tyr Ile Asp Gly Leu Cys Gly Gly Glu Leu Pro Leu Thr Gly
    275                 280                 285

Met Arg Thr Ala Ser Ser Ile Ala Phe Asn Val Leu Lys Lys Met Thr
290                 295                 300

Phe Gly Glu Glu Lys Thr Glu Glu Gly Tyr Ile Asn Tyr Phe Glu Leu
305                 310                 315                 320

Asp Lys Lys Thr Lys Phe Glu Phe Leu Arg Lys Arg Ile Glu Met Glu
                325                 330                 335

Ser Tyr Thr Gly Gly Tyr Thr His Ala Asn His Lys Ala Val Gly Lys
            340                 345                 350

Thr Ile Asn Lys Ile Gly Cys Ser Leu Asp Ile Asn Ser Ser Tyr Pro
        355                 360                 365

Ser Gln Met Ala Tyr Lys Val Phe Pro Tyr Gly Lys Pro Val Arg Lys
370                 375                 380

Thr Trp Gly Arg Lys Pro Lys Thr Glu Lys Asn Glu Val Tyr Leu Ile
385                 390                 395                 400

Glu Val Gly Phe Asp Phe Val Glu Pro Lys His Glu Glu Tyr Ala Leu
                405                 410                 415

Asp Ile Phe Lys Ile Gly Ala Val Asn Ser Lys Ala Leu Ser Pro Ile
            420                 425                 430

Thr Gly Ala Val Ser Gly Gln Glu Tyr Phe Cys Thr Asn Ile Lys Asp
        435                 440                 445

Gly Lys Ala Ile Pro Val Tyr Lys Glu Leu Lys Asp Thr Lys Leu Thr
450                 455                 460

Thr Asn Tyr Asn Val Val Leu Thr Ser Val Glu Tyr Glu Phe Trp Ile
465                 470                 475                 480

Lys His Phe Asn Phe Gly Val Phe Lys Lys Asp Glu Tyr Asp Cys Phe
                485                 490                 495

Glu Val Asp Asn Leu Glu Phe Thr Gly Leu Lys Ile Gly Ser Ile Leu
            500                 505                 510

Tyr Tyr Lys Ala Glu Lys Gly Lys Phe Lys Pro Tyr Val Asp His Phe
        515                 520                 525

Thr Lys Met Lys Val Glu Asn Lys Lys Leu Gly Asn Lys Pro Leu Thr
530                 535                 540

Asn Gln Ala Lys Leu Ile Leu Asn Gly Ala Tyr Gly Lys Phe Gly Thr
545                 550                 555                 560

Lys Gln Asn Lys Glu Glu Lys Asp Leu Ile Met Asp Lys Asn Gly Leu
                565                 570                 575

Leu Thr Phe Thr Gly Ser Val Thr Glu Tyr Glu Gly Lys Glu Phe Tyr
            580                 585                 590

Arg Pro Tyr Ala Ser Phe Val Thr Ala Tyr Gly Arg Leu Gln Leu Trp
        595                 600                 605

Asn Ala Ile Ile Tyr Ala Val Gly Val Glu Asn Phe Leu Tyr Cys Asp
610                 615                 620

Thr Asp Ser Ile Tyr Cys Asn Arg Glu Val Asn Ser Leu Ile Glu Asp
625                 630                 635                 640
```

```
Met Asn Ala Ile Gly Glu Thr Ile Asp Lys Thr Ile Leu Gly Lys Trp
            645                 650                 655

Asp Val Glu His Val Phe Asp Lys Phe Lys Val Leu Gly Gln Lys Lys
            660                 665                 670

Tyr Met Tyr His Asp Cys Lys Glu Asp Lys Thr Asp Leu Lys Cys Cys
            675                 680                 685

Gly Leu Pro Ser Asp Ala Arg Lys Ile Ile Ile Gly Gln Gly Phe Asp
            690                 695                 700

Glu Phe Tyr Leu Gly Lys Asn Val Glu Gly Lys Gln Arg Lys Lys
705                 710                 715                 720

Val Ile Gly Gly Cys Leu Leu Leu Asp Thr Leu Phe Thr Ile Lys Lys
            725                 730                 735

Ile Met Phe

<210> SEQ ID NO 3
<211> LENGTH: 2220
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
atgcatcacc atcatcatca ccaccacagc ggcggttccg acaaacacac gcagtacgtc      60
aaagagcata gcttcaatta tgacgagtat aagaaagcga atttcgacaa gatcgagtgc     120
ctgatctttg acaccgagag ctgcacgaat tatgagaacg ataataccgg tgcacgtgtt     180
tacggttggg gtcttggcgt cacccgcaac acaatatga tctacggcca aaatctgaat      240
cagttttggg aagtatgcca gaacattttc aatgattggt atcacgacaa caaacatacc     300
attaagatta ccaagaccaa gaaaggcttc ccgaaacgta agtacattaa gtttccgatt     360
gcagttcaca atttgggctg ggatgttgaa ttcctgaagt atagcctggt ggagaatggt     420
ttcaattacg acaagggtct gctgaaaact gtttttagca agggtgcgcc gtaccaaacc     480
gtgaccgatg ttgaggaacc gaaaacgttc atatcgtcc agaataacaa catcgtttat      540
ggttgtaacg tgtatatgga caaattcttt gaggtcgaga caaagacgg ctctaccacc      600 gagattggcc tgtgcttgga tttcttcgat agctataaga tcatcacgtg tgctgagagc     660
cagttccaca attacgttca tgatgtggat ccaatgttct acaaaatggg tgaagagtat     720
gattacgata cttggcgtag cccgacgcac aagcagacca ccctggagct gcgctaccaa     780
tacaatgata tctatatgct gcgtgaagtc atcgaacagt tttacattga cggtttatgt     840
ggcggcgagc tgccgctgac cggcatgcgc accgcttcca gcattgcgtt caacgtgctg     900
aaaaagatga cctttggtga ggaaaagacg aagagggct acatcaacta ttttgaattg     960
gacaagaaaa ccaaattcga gtttctgcgt aagcgcattg aaatggaatc gtacaccggt    1020
ggctatacgc acgcaaatca caagccgtt ggtaagacta ttaacaagat cggttgctct    1080
ttggacatta acagctcata ccctttcgcag atggcgtaca aggtctttcc gtatggcaaa    1140
ccggttcgta agacctgggg tcgtaaacca aagaccgaga agaacgaagt ttatctgatt    1200
gaagttggct tgacttcgt ggagccgaaa acgaagaat acgcgctgga tatctttaag     1260
attggtgcgg tgaactctaa agcgctgagc ccgatcaccg cgctgtcag cggtcaagag    1320 tatttctgta cgaacattaa agacggcaaa gcaatcccgg tttacaaaga actgaaggac    1380
accaaattga ccactaacta caatgtcgtg ctgaccagcg tggagtacga gttctggatc    1440
```

```
aaacacttca atttggtgt gtttaagaaa gacgagtacg actgtttcga agttgacaat    1500
ctggagttta cgggtctgaa gattggttcc attctgtact acaaggcaga gaaaggcaag    1560
tttaaacctt acgtggatca cttcacgaaa atgaaagtgg agaacaagaa actgggtaat    1620
aagccgctga cgaatcaggc aaagctgatt ctgaacggtg cgtacggcaa attcggcacc    1680
aaacaaaaca aagaagagaa agatttgatc atggataaga acggtttgct gaccttcacg    1740
ggtagcgtca cggaatacga gggtaaagaa ttctatcgtc cgtatgcgag cttcgttact    1800
gcctatggtc gcctgcaact gtggaacgcg attatctacg cggttggtgt ggagaatttt    1860
ctgtactgcg acaccgacag catctattgt aaccgtgaag ttaacagcct cattgaggat    1920
atgaacgcca ttggtgaaac catcgataaa acgattctgg gtaaatggga cgtggagcat    1980
gtctttgata agtttaaggt cctgggccag aagaagtaca tgtatcatga ttgcaaagaa    2040
gataaaacgg acctgaagtg ttgcggtctg ccgagcgatg cccgtaagat tatcattggt    2100
caaggtttcg acgagttta tctgggcaaa aatgtcgaag gtaagaagca acgcaaaaaa    2160
gtgatcggcg gttgcctgct gctggacacc ctgtttacga tcaagaaaat catgttctaa    2220

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE
<221> NAME/KEY: MISC_FEATURE
<222> LOCATION: (1)..(15)
<223> OTHER INFORMATION: This sequence may encompass 1 to 3 'Gly Gly
      Gly Gly Ser' repeating units, wherein some positions may be absent

<400> SEQUENCE: 4

Gly Gly Gly Gly Ser Gly Gly Gly Gly Ser Gly Gly Gly Gly Ser
1               5                   10                  15

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Ser Lys Leu Gly
1               5

<210> SEQ ID NO 6
<211> LENGTH: 131
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
tatgatgata gtagtagtcg attcaggaac agatctccag tggaacagat ctccagttga     60
acagatctcc ttactggaga tctgttcaac tggagatctg ttccactgga gatctgttcc    120
tgaatcaaaa a                                                         131

<210> SEQ ID NO 7
<211> LENGTH: 84
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tatgatgata gtagtagtcg attcaggaac agatctccag tggaacagat ctccagttga    60
acagatctcc ttactggaga tctg                                           84

<210> SEQ ID NO 8
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tatgatatgt agtaagtcga tttaggcaga tctgtgaaac agactccagt tgaacgatct    60
tgagattcg                                                            69

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tttttttttt tttttttttt tttttttttt                                     30
```

POLYMERASE VARIANTS AND USES THEREOF

CROSS-REFERENCE TO RELATED APPLICATIONS

This is a Continuation of U.S. Ser. No. 16/694,985, (filed Nov. 25, 2019), which is a Continuation of U.S. patent application Ser. No. 15/151,364 (filed May 10, 2016), which is a Continuation-in-Part of U.S. application Ser. No. 15/012,317 (filed Feb. 1, 2016 and issued as U.S. Pat. No. 10,308,918 B2 on Jun. 4, 2019), which claims priority to U.S. Provisional Patent Application 62/161,571 (filed on May 14, 2015) and U.S. Provisional Patent Application 62/202,895 (filed on Aug. 9, 2015). Each of the foregoing patents and patent applications is hereby incorporated by reference in its entirety.

SEQUENCE LISTING

The instant application contains a Sequence Listing which has been filed electronically in ASCII format and is hereby incorporated by reference in its entirety. Said ASCII copy, created on Mar. 3, 2021, is named P32651US8_SL_ST25 and is 18,052 bytes in size.

TECHNICAL FIELD

Provided herein, among other things, are modified DNA polymerases containing amino acid alterations based on mutations identified in directed evolution experiments designed to select enzymes that are better suited for applications in recombinant DNA technologies.

BACKGROUND

DNA polymerases are a family of enzymes that use single-stranded DNA as a template to synthesize the complementary DNA strand. In particular, DNA polymerases can add free nucleotides to the 3' end of a newly-forming strand resulting in elongation of the new strand in a 5' to 3' direction. Most DNA polymerases are multifunctional proteins that possess both polymerizing and exonucleolytic activities. For example, many DNA polymerases have 3'→5' exonuclease activity. These polymerases can recognize an incorrectly incorporated nucleotide and the 3'→5' exonuclease activity of the enzyme allows the incorrect nucleotide to be excised (this activity is known as proofreading). Following nucleotide excision, the polymerase can re-insert the correct nucleotide and replication can continue. Many DNA polymerases also have 5'→3' exonuclease activity.

Polymerases have found use in recombinant DNA applications, including nanopore sequencing. However, a DNA strand moves rapidly at the rate of 1 μs to 5 μs per base through the nanopore. This makes recording difficult and prone to background noise, failing in obtaining single-nucleotide resolution. Therefore, the use of detectable tags on nucleotides may be used in the sequencing of a DNA strand or fragment thereof. Thus, there is a not only a need to control the rate of DNA being sequenced but also provide polymerases that have improved properties (relative to the wild-type enzyme) such as incorporation of modified nucleotides, e.g., polyphosphate nucleotides with or without tags.

BRIEF SUMMARY OF THE INVENTION

The present invention provides modified DNA polymerases (e.g., mutants) based on directed evolution experiments designed to select mutations that confer advantageous phenotypes under conditions used in industrial or research applications, e.g., catalyzing incorporation of modified polyphosphate nucleotides, e.g., tagged nucleotides, under high salt concentrations.

In an aspect there is a variant polymerase comprising at least one alteration at a position corresponding to of H223, N224, Y225, H227, I295, Y342, T343, I357, S360, L361, I363, S365, S366, Y367, P368, D417, E475, Y476, F478, K518, H527, T529, M531, N535, G539, P542, N545, Q546, A547, L549, I550, N552, G553, F558, A596, G603, A610, V615, Y622, C623, D624, I628, Y629, R632, N635, M641, A643, I644, T647, I648, T651, I652, K655, W656, D657, V658, H660, F662, and L690 of SEQ ID NO:2 (Pol6 (with His tag)).

In one embodiment there is provided a modified DNA polymerase having a DNA polymerase activity comprising an amino acid sequence having at least 70%, at least 75%, at least 80%, at least 90% or at least 95% sequence identity to the amino acid sequence as set forth in SEQ ID NO: 1 or 2.

In a second embodiment there is provided a modified DNA polymerase having a DNA polymerase activity comprising an amino acid sequence having at least 70%, at least 75%, at least 80%, at least 90% or at least 95% sequence identity to the amino acid sequence as set forth in SEQ ID NO: 1 or 2 having one or more amino acid substitutions selected from the group consisting of H223, N224, Y225, H227, I295, Y342, T343, I357, S360, L361, I363, S365, S366, Y367, P368, D417, E475, Y476, F478, K518, H527, T529, M531, N535, G539, P542, N545, Q546, A547, L549, I550, N552, G553, F558, A596, G603, A610, V615, Y622, C623, D624, I628, Y629, R632, N635, M641, A643, I644, T647, I648, T651, I652, K655, W656, D657, V658, H660, F662, and L690 and combinations thereof. In a further embodiment, the one or more amino acid substitutions are selected from H223A, N224Y/L/Q/M/R/K, Y225L/T/I/F/A/M, H227P/E/F/Y, I295W/F/M/E, Y342L/F, T343N/F, I357G/L/Q/H/W/M/A/E/Y/P, S360G/E/Y, L361M/W/V/F, I363V/A/R/M/W, S365Q/W/M/A/G, S366A/L, Y367L/E/M/P/N/F, P368G, D417P, E475D, Y476V, F478L, K518Q, H527W/R/L/Y/T/M, T529M/F, M531H/Y/A/K/R/W/T/L/V/G, N535L/Y/M/K/I/R/W/Q, G539Y/F, P542E/S/G, N545K/D/S/L/R/Q/W, Q546W/F, A547M/Y/W/F/V/S, L549Q/Y/H/G/R/K, I550A/W/T/G/F/S, N552L/M/S/T, G553S/T/E/Q/K/R/M, F558P/T, A596S, G603T/A/L, A610T/E, V615A/T, Y622A/M, C623G/S/Y/F, D624F/K, I628Y/V/F/L/M, Y629W/H/M/K, R632L/C, N635D, M641 L/Y, A643L, I644H/M/Y, T647G/A/E/K/S/Y, I648K/R/V/N/T/L, T651Y/F/M, I652Q/G/S/N/F/T/A/L/E/K/M, K655G/F/E/N/Q/M/A, W656E, D657R/P/A/E, V658L, H660A/Y, F662I/L, L690M and combinations thereof. The modified DNA polymerase having one or more amino acid substitutions has an altered characteristic selected from enzyme activity, fidelity, processivity, elongation rate, sequencing accuracy, long continuous read capability, stability, and solubility relative to the parental polymerase. In an embodiment, the altered characteristic is enzyme activity. In an embodiment, the altered characteristic is fidelity. In an embodiment, the altered characteristic is processivity. In an embodiment, the altered characteristic is elongation rate. In an embodiment, the altered characteristic is stability. In an embodiment, the altered characteristic is solubility. In one embodiment, the altered characteristic is an ability to bind and/or incorporate polyphosphate nucleotides, e.g., a tetraphosphate, pentaphosphate, hexaphosphate, heptaphosphate or octophosphate nucleotide.

In a third embodiment, there is provided a modified DNA polymerase having an altered characteristic selected from enzyme activity, fidelity, processivity, elongation rate, stability, or solubility, when compared to SEQ ID NO:1 or 2. In an embodiment, the altered characteristic is enzyme activity. In an embodiment, the altered characteristic is fidelity. In an embodiment, the altered characteristic is processivity. In an embodiment, the altered characteristic is elongation rate. In an embodiment, the altered characteristic is stability. In an embodiment, the altered characteristic is solubility.

In a fourth embodiment, there is provided a modified DNA polymerase having a DNA polymerase activity comprising an amino acid sequence having at least 70%, at least 75%, at least 80%, at least 90% or at least 95% sequence identity to the amino acid sequence as set forth in SEQ ID NO: 1, which amino acid sequence includes one or more amino acid substitutions, such substitutions being selected from the group consisting of H223A, N224Y/L/Q/M/R/K, Y225L/T/I/F/A, H227P/E/F/Y, I295W/F/M/E, Y342L/F, T343N/F, I357G/L/Q/H/W/M/A/E/Y/P, S360G/E/Y, L361M/W/V/F, I363V/A/R/M/W, S365Q/W/M/A/G, S366A/L, Y367L/E/M/P/N/F, P368G, D417P, E475D, Y476V, F478L, K518Q, H527W/R/L/Y/T/M, T529M/F, M531H/Y/A/K/R/W/T/L/V/G, N535L/Y/M/K/I/R/W/Q, G539Y/F, P542E/S/G, N545K/D/S/L/R/Q/W, Q546W/F, A547M/Y/W/F/V/S, L549Q/Y/H/G/R/K, I550A/W/T/G/F/S, N552L/M/S/T, G553S/T/E/Q/K/R/M, F558P/T, A596S, G603T/A/L, A610T/E, V615A/T, Y622A/M, C623G/S/Y/F, D624F/K, I628Y/V/F/L/M, Y629W/H/M/K, R632L/C, N635D, M641L/Y, A643L, I644H/M/Y, T647G/A/E/K/S/Y, I648K/R/V/N/T/L, T651Y/F/M, I652Q/G/S/N/F/T/A/L/E/K/M, K655G/F/E/N/Q/M/A, W656E, D657R/P/A/E, V658L, H660A/Y, F662I/L, L690M and combinations thereof, wherein the one or more amino acid substitutions alter enzyme activity, fidelity, processivity, elongation rate, sequencing accuracy, long continuous read capability, stability, or solubility relative to the parental polymerase. In an embodiment, the altered characteristic is enzyme activity. In an embodiment, the altered characteristic is fidelity. In an embodiment, the altered characteristic is processivity. In an embodiment, the altered characteristic is elongation rate. In an embodiment, the altered characteristic is stability. In an embodiment, the altered characteristic is solubility. In one embodiment, the altered characteristic is an ability to bind and/or incorporate polyphosphate nucleotides, e.g., a tetraphosphate, pentaphosphate, hexaphosphate, heptaphosphate or octophosphate nucleotide.

In an embodiment, the variant polymerase having altered enzyme activity as compared to SEQ ID NO: 1 or 2 is selected from a. H223A;
b. N224Y/L/Q/M/R/K;
c. Y225L/I/T/F/A/M;
d. H227P/E/F/Y;
e. I295F/E/M/W;
f. Y342L/F;
g. T343N/F;
h. I357G/L/Q/H/W/M/A/E/Y/P;
i. S360G/E/Y;
j. L361M/W/V/F;
k. I363V/A/R/M/W;
l. S365Q/W/M/A/G;
m. S366A/L;
n. Y367L/E/M/P/N/F;
o. P368G;
p. D417P;
q. E475D;
r. Y476V;
s. F478L;
t. K518Q;
u. H527W/R/L/Y/T/M;
v. T529M/F;
w. M531H/Y/A/K/R/W/T/L/V/G;
x. N535L/Y/M/K/I/R/W/Q;
y. P542E/S/G;
z. N545D/K/S/L/R/Q/W;
aa. Q546W/F;
bb. A547F/M/W/Y/V/S;
cc. L549H/Y/Q/G/R/K;
dd. I550A/W;
ee. I550T/G/F/S;
ff. N552L/M/T;
gg. G553S/T/E/Q/K/R/M;
hh. F558P/T;
ii. A596S;
jj. G603T/A/L;
kk. A610T/E;
ll. V615A/T;
mm. Y622A/M;
nn. C623G/S/Y/A/F;
oo. D624F/K;
pp. I628Y/V/F/L/M;
qq. Y629W/H/M/K;
rr. R632L/C;
ss. N635D;
tt. M641L/Y;
uu. A643L;
vv. I644H/M/Y;
ww. T647G/A/E/K/S/Y;
xx. I648K/R/V/N/T/L;
yy. T651Y/F/M;
zz. I652Q/G/S/N/F/T/A/L/E/K/M;
aaa. K655G/F/E/N/Q/M/A;
bbb. W656E;
ccc. D657R/P/A/E;
ddd. V658L;
eee. H660A/Y;
fff. F662I/L;
ggg. L690M;
hhh. S366A+N535L;
iii. T651Y+N535L;
jjj. Y342L+E475D+F478L;
kkk. T343N+D417P+K518Q;
lll. N535L+N545K+T651Y;
mmm. I363V+E475D+Y476V;
nnn. S366L+G553S+F558P;
ooo. S366A+N535L+A547M;
ppp. S366A+P542E+N545K;
qqq. S366A+P542E+I652Q;
rrr. S366A+N535L+T529M;
sss. S366A+N535L+I652Q;
ttt. S366A+N535L+N545K;
uuu. T651Y+P542E+N545K;
vvv. I651Y+P542E+Q546W;
www. I651Y+P542E+S366A;
xxx. I651Y+N535L+N545K;
yyy. S366A+N535I+I652Q;
zzz. I651Y+S366A+A547F;
aaaa. T647G+A547F+Y225T;
bbbb. A547F+A610T+S366A;
cccc. A547F+A610T+Y225I;
dddd. S366A+T647G+A547F;
eeee. T529M+S366A+A547F;

ffff. T647E+S366A+A547F;
gggg. T529M+T647G+A547F;
hhhh. N545K+S366A+A547F;
iiii. T647G+A547F+T529M;
jjjj. T529M+A610T+A547F;
kkkk. M641Y+T529M+A547F;
llll. I647G+O623G+A547F;
mmmm. A610T+I295W+T651Y;
nnnn. V615A+M531Y+T647G;
oooo. S366L+F478L+A596S+L690M;
pppp. H223A+G553S+A643L+F662I;
qqqq. N535L+N545K+T651Y+T529M;
rrrr. N535L+N545K+T651Y+N635D;
ssss. N535L+N545K+T651Y+I652Q;
tttt. S366A+N535L+I652Q+T529M;
uuuu. S366A+S365A+P368G+G603T;
vvvv. N535L+N545K+T651Y+T647G;
wwww. S366A+N535L+I652Q+A547Y;
xxxx. S366A+N535L+A547M+T647G;
yyyy. T529M+S366A+A547F+N545K;
zzzz. T529M+S366A+A547F+N545R;
aaaaa. T529M+S366A+A547F+N552L;
bbbbb. T529M+S366A+A547F+Y629W;
ccccc. N535I+N545K+T651Y+T529M;
ddddd. N535I+N545K+T651Y+N635D;
eeeee. N535I+N545K+T651Y+I652Q;
fffff. N535L+N545K+T651Y+T647G+C623G;
ggggg. N535L+N545K+T651Y+T647G+I628Y;
hhhhh. S366A+N535L+A547M+T647G+S360G;
iiiii. N535I+N545K+T651Y+I652Q+Y225I;
jjjjj. N535L+N545K+T651Y+T647G+K655G;
kkkkk. N535L+N545K+T651Y+T647G+L549O;
lllll. S366A+N535L+I6520+A547Y+K655G;
mmmmm. T529M+S366A+A547F+N545L+Y629W;
nnnnn. T529M+S366A+A547F+N545L+Y225L;
ooooo. T529M+S366A+A547F+N545L+Y225F;
ppppp. T529M+S366A+A547F+N545L+K655F;
qqqqq. T529M+S366A+A547F+N545L+N552L;
rrrrr. T529M+S366A+A547F+N545R+M531A;
sssss. T529M+S366A+A547F+N545R+G539Y;
ttttt. T529M+S366A+A547F+N545R+V658L;
uuuuu. T529M+S366A+A547F+N545L+Y225L+D657R;
vvvvv. T529M+S366A+A547F+N545L+Y225L+N552L;
wwwww. T529M+S366A+A547F+N545L+Y225L+I652G;
xxxxx. T529M+S366A+A547F+N545L+Y225L+I652Q;
yyyyy. T529M+S366A+A547F+N545L+Y225L+N552M
zzzzz. T529M+S366A+A547F+N545L+Y225L+D657R+N224R;
aaaaaa. T529M+S366A+A547F+N545L+Y225L+D657R+I628M;
bbbbbb. T529M+S366A+A547F+N545L+Y225L+D657R+K655A; and
cccccc. T529M+S366A+A547F+N545L+Y225L+D657R+Y629W.

In an embodiment, the altered characteristic is enzyme activity. In an embodiment, the altered characteristic is fidelity. In an embodiment, the altered characteristic is processivity. In an embodiment, the altered characteristic is elongation rate. In an embodiment, the altered characteristic is stability. In an embodiment, the altered characteristic is solubility. In one embodiment, the altered characteristic is an ability to bind and/or incorporate polyphosphate nucleotides, e.g., a tetraphosphate, pentaphosphate, hexaphosphate, heptaphosphate or octophosphate nucleotide.

In some embodiments, the variant polymerase having altered enzyme activity, as compared to SEQ ID NO: 2 having the N535I+N545K+T651Y+N635D mutations, or SEQ ID NO: 1 or 2 is selected from
a. A547F+A610T+Y225I;
b. Y225T+T647G+A547F;
c. S366A+T647G+A547F;
d. S366A+A547F+A610T;
e. T529M+S366A+A547F;
f. T529M+T647G+A547F;
g. T529M+A610T+A547F;
h. N545K+S366A+A547F;
i. N545K+T647G+A547F;
j. A610T+I295W+T651Y;
k. V615A+M531Y+T647G;
l. M641Y+T529M+A547F;
m. T647E+S366A+A547F;
n. T647G+A547F+T529M;
o. T647G+C623G+A547F; and
p. T651Y+S366A+A547F.

In some embodiments, the variant polymerase is selected from
a. N535L+N545K+T651Y;
b. S366A+N535L+I652Q;
c. S366A+T529M+N535L;
d. S366A+N535L+N545K;
e. S366A+N535L+A547M;
f. S366A+P542E+I652Q;
g. S366A+P542E+N545K;
h. S366A+P542E+T651Y;
i. P542E+N545K+T651Y;
j. P542E+Q546W+T651Y;
k. N535L+T651Y;
l. S366A+N535L;
m. N535L+N545K+T651Y+T529M;
n. N535L+N545K+T651Y+N635D;
o. N535L+N545K+T651Y+I652O;
p. S366A+N535L+I652O+T529M;
q. N535L+N545K+T651Y+T647G;
r. S366A+N535L+I652O+A547Y;
s. S366A+N535L+A547M+T647G;
t. S366A+N535L+I652O;
u. N535I+N545K+T651Y+T529M;
v. N535I+N545K+T651Y+N635D;
w. N535I+N545K+T651Y+I652Q;
x. N535L+N545K+T651Y+T647G+C623G;
y. N535L+N545K+T651Y+T647G+I628Y;
z. S366A+N535L+A547M+T647G+S360G;
aa. N535I+N545K+T651Y+I652Q+Y225I;
bb. N535L+N545K+T651Y+T647G+K655G;
cc. N535L+N545K+T651Y+T647G+L549O;
dd. S366A+N535L+I652Q+A547Y+K655G;
ee. T647G+A547F+Y225T;
ff. A547F+A610T+S366A;
gg. A547F+A610T+Y225I;
hh. S366A+T647G+A547F;
ii. I651Y+S366A+A547F;
jj. T529M+S366A+A547F;
kk. T647E+S366A+A547F;
ll. T529M+T647G+A547F;
mm. N545K+S366A+A547F;
nn. T647G+A547F+T529M;
oo. N545K+T647G+A547F;
pp. T529M+A610T+A547F;
qq. M641Y+T529M+A547F;
rr. T647G+C623G+A547F;
ss. A610T+I295W+T651Y;

tt. V615A+M531Y+T647G;
uu. T529M+S366A+A547F+N545K;
vv. T529M+S366A+A547F+N545R;
ww. T529M+S366A+A547F+N552L;
xx. T529M+S366A+A547F+Y629W;
yy. T529M+S366A+A547F+N545L+Y629W;
zz. T529M+S366A+A547F+N545L+Y225L;
aaa. T529M+S366A+A547F+N545L+Y225F;
bbb. T529M+S366A+A547F+N545L+K655F;
ccc. T529M+S366A+A547F+N545L+N552L;
ddd. T529M+S366A+A547F+N545R+M531A;
eee. T529M+S366A+A547F+N545R+G539Y;
fff. T529M+S366A+A547F+N545R+V658L;
ggg. T529M+S366A+A547F+N545L+Y225L+D657R;
hhh. T529M+S366A+A547F+N545L+Y225L+N552L;
iii. T529M+S366A+A547F+N545L+Y225L+I652G;
jjj. T529M+S366A+A547F+N545L+Y225L+I652Q;
kkk. T529M+S366A+A547F+N545L+Y225L+N552M
lll. T529M+S366A+A547F+N545L+Y225L+D657R+ N224R;
mmm. T529M+S366A+A547F+N545L+Y225L+ D657R+I628M;
nnn. T529M+S366A+A547F+N545L+Y225L+D657R+ K655A; and
ooo. T529M+S366A+A547F+N545L+Y225L+D657R+ Y629W.

In some embodiments, the variant polymerase having altered enzyme activity as compared to SEQ ID NOs: 1 or 2, or the parental polymerase.

In some embodiments, the variant polymerase having altered enzyme activity, as compared to SEQ ID NO: 2 having the S366A+T529M+N545L+A547F mutations, or SEQ ID NO:1 or 2, is selected from
a. Y225L/F/A/M;
b. M531A/G;
c. G539Y;
d. N552L/T;
e. Y629W/K;
f. K655F.

In an embodiment, the altered characteristic is enzyme activity. In an embodiment, the altered characteristic is fidelity. In an embodiment, the altered characteristic is processivity. In an embodiment, the altered characteristic is elongation rate. In an embodiment, the altered characteristic is stability. In an embodiment, the altered characteristic is solubility. In one embodiment, the altered characteristic is an ability to bind and/or incorporate polyphosphate nucleotides, e.g., a tetraphosphate, pentaphosphate, hexaphosphate, heptaphosphate or octophosphate nucleotide.

In some embodiments, the parental polymerase is wild-type Pol6 (SEQ ID NO:1). In some embodiments, the parental polymerase is Pol6 comprising a His-tag (SEQ ID NO:2). In some embodiments, the parental polymerase is comprises the mutations S366A+T529M+A547F+N545L/ R. In some embodiments, the parental polymerase may be SEQ ID NO:1 comprising one or more mutations. For example, S366A+T529M+A547F+N545R used S366A+ T529M+A547F as the parental polymerase then added N545R.

In some embodiments, the modified polymerase has a $k_{chem}$ that is greater than the parental polymerase. In some embodiments, the modified polymerase has a $k_{off}$ that is less than the parental polymerase. In some embodiments, the modified polymerase has a $k_{chem}/k_{off}$ (i.e., a ratio) that is at least 1.5, 2.0 or 2.5 times greater than the parental polymerase.

Other objects, features and advantages of the present invention will become apparent from the following detailed description. It should be understood, however, that the detailed description and specific examples, while indicating preferred embodiments of the invention, are given by way of illustration only, since various changes and modifications within the scope and spirit of the invention will become apparent to one skilled in the art from this detailed description.

BRIEF DESCRIPTION OF THE DRAWINGS

FIG. 2 shows a schematic of the $k_{chem}$ assay used herein to measure the rate of incorporation of polyphosphates. Reference is made to Example 6.

FIG. 3 is a summary of the fluorescence quenching based $k_{off}$ assay used herein to measure kinetic properties of the variant polymerases. Reference is made to Example 4.

DETAILED DESCRIPTION

Figure 1:
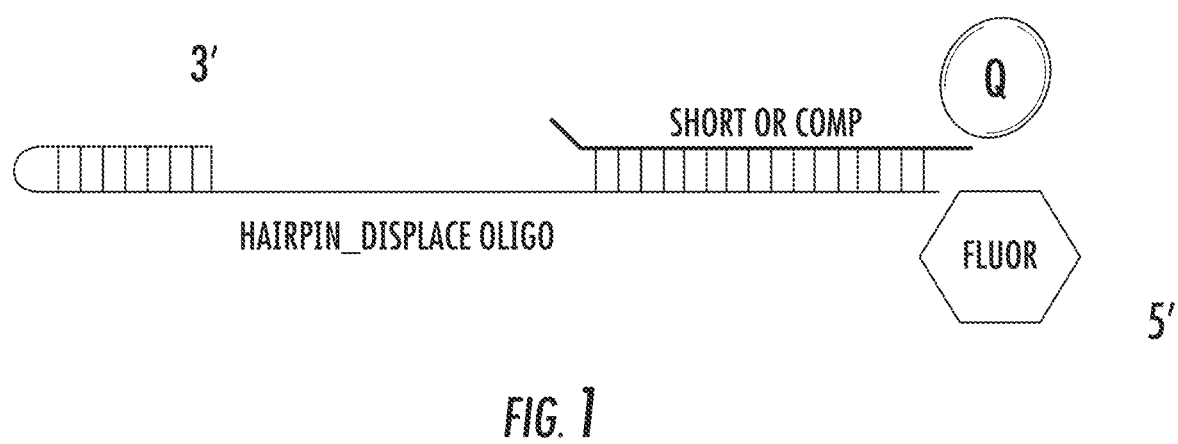
FIG. 1 illustrates an exemplary template used in the displacement assay. Reference is made to Example 3.

The invention will now be described in detail by way of reference only using the following definitions and examples. All patents and publications, including all sequences disclosed within such patents and publications, referred to herein are expressly incorporated by reference.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, N.Y. (1991) provide one of skill with a general dictionary of many of the terms used in this invention. Although any methods and materials similar or equivalent to those described herein can be used in the practice or testing of the present invention, preferred methods and materials are described. Practitioners are particularly directed to Sambrook et al., 1989, and Ausubel F M et al., 1993, for definitions and terms of the art. It is to be understood that this invention is not limited to the particular methodology, protocols, and reagents described, as these may vary.

Numeric ranges are inclusive of the numbers defining the range. The term about is used herein to mean plus or minus ten percent (10%) of a value. For example, "about 100" refers to any number between 90 and 110.

Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention which can be had by reference to the specification as a whole. Accordingly, the terms defined immediately below are more fully defined by reference to the specification as a whole.

Definitions

Amino acid: As used herein, the term "amino acid," in its broadest sense, refers to any compound and/or substance that can be incorporated into a polypeptide chain. In some embodiments, an amino acid has the general structure $H_2N—C(H)(R)—COOH$. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, and/or substitution with other chemical without adversely affecting their activity. Amino acids may participate in a disulfide bond. The term "amino acid" is used interchangeably with "amino acid residue," and may refer to a free amino acid and/or to an amino acid residue of a peptide. It will be apparent from the context in which the term is used whether it refers to a free amino acid or a residue of a peptide. It should be noted that all amino acid residue sequences are represented herein by formulae whose left and right orientation is in the conventional direction of amino-terminus to carboxy-terminus.

Base Pair (bp): As used herein, base pair refers to a partnership of adenine (A) with thymine (T), or of cytosine (C) with guanine (G) in a double stranded DNA molecule.

Complementary: As used herein, the term "complementary" refers to the broad concept of sequence complementarity between regions of two polynucleotide strands or between two nucleotides through base-pairing. It is known that an adenine nucleotide is capable of forming specific hydrogen bonds ("base pairing") with a nucleotide which is thymine or uracil. Similarly, it is known that a cytosine nucleotide is capable of base pairing with a guanine nucleotide.

DNA binding affinity: As used herein, the term "DNA-binding affinity" typically refers to the activity of a DNA polymerase in binding DNA nucleic acid. In some embodiments, DNA binding activity can be measured in a two band-shift assay. See, e.g., Sambrook et al. (2001) Molecular Cloning: A Laboratory Manual ($3^{rd}$ ed., Cold Spring Harbor Laboratory Press, NY) at 9.63-9.75 (describing end-labeling of nucleic acids). A reaction mixture is prepared containing at least about 0.5 μg of the polypeptide in about 10 μl of binding buffer (50 mM sodium phosphate buffer (pH 8.0), 10% glycerol, 25 mM KCl, 25 mM $MgCl_2$). The reaction mixture is heated to 37° C. for 10 min. About $1 \times 10^4$ to $5 \times 10^4$ cpm (or about 0.5-2 ng) of the labeled double-stranded nucleic acid is added to the reaction mixture and incubated for an additional 10 min. The reaction mixture is loaded onto a native polyacrylamide gel in 0.5× Tris-borate buffer. The reaction mixture is subjected to electrophoresis at room temperature. The gel is dried and subjected to autoradiography using standard methods. Any detectable decrease in the mobility of the labeled double-stranded nucleic acid indicates formation of a binding complex between the polypeptide and the double-stranded nucleic acid. Such nucleic acid binding activity may be quantified using standard densitometric methods to measure the amount of radioactivity in the binding complex relative to the total amount of radioactivity in the initial reaction mixture. Other methods of measuring DNA binding affinity are known in the art (see, e.g., Kong et al. (1993) J. Biol. Chem. 268(3):1965-1975).

Elongation rate: As used herein, the term "elongation rate" refers to the average rate at which a DNA polymerase extends a polymer chain. As used herein, a high elongation rate refers to an elongation rate higher than 2 nt/s (e.g., higher than 30, 35, 40, 45, 50, 55, 60, 65, 70, 75, 80, 85, 90, 95, 100, 105, 110, 115, 120, 125, 130, 135, 140 nt/s). As used in this application, the terms "elongation rate", "extension rate" and "incorporation rate" are used inter-changeably.

Enzyme activity: As used herein, the term "enzyme activity" refers to the specificity and efficiency of a DNA polymerase. Enzyme activity of a DNA polymerase is also referred to as "polymerase activity," which typically refers to the activity of a DNA polymerase in catalyzing the template-directed synthesis of a polynucleotide. Enzyme activity of a polymerase can be measured using various techniques and methods known in the art. For example, serial dilutions of polymerase can be prepared in dilution buffer (e.g., 20 mM Tris.Cl, pH 8.0, 50 mM KCl, 0.5% NP 40, and 0.5% Tween-20). For each dilution, 5 µl can be removed and added to 45 µl of a reaction mixture containing 25 mM TAPS (pH 9.25), 50 mM KCl, 2 mM $MgCl_2$, 0.2 mM dATP, 0.2 mM dGTP, 0.2 mM dTTP, 0.1 mM dCTP, 12.5 µg activated DNA, 100 µM [$\alpha$-$^{32}$P]dCTP (0.05 µCi/nmol) and sterile deionized water. The reaction mixtures can be incubated at 37° C. (or 74° C. for thermostable DNA polymerases) for 10 minutes and then stopped by immediately cooling the reaction to 4° C. and adding 10 µl of ice-cold 60 mM EDTA. A 25 µl aliquot can be removed from each reaction mixture. Unincorporated radioactively labeled dCTP can be removed from each aliquot by gel filtration (Centri-Sep, Princeton Separations, Adelphia, N.J.). The column eluate can be mixed with scintillation fluid (1 ml). Radioactivity in the column eluate is quantified with a scintillation counter to determine the amount of product synthesized by the polymerase. One unit of polymerase activity can be defined as the amount of polymerase necessary to synthesize 10 nmole of product in 30 minutes (Lawyer et al. (1989) *J. Biol. Chem.* 264:6427-647). Other methods of measuring polymerase activity are known in the art (see, e.g. Sambrook et al. (2001) Molecular Cloning: A Laboratory Manual (3rd ed., Cold Spring Harbor Laboratory Press, NY)).

Purified: As used herein, "purified" means that a molecule is present in a sample at a concentration of at least 90% by weight, or at least 95% by weight, or at least 98% by weight of the sample in which it is contained.

Isolated: An "isolated" molecule is a nucleic acid molecule that is separated from at least one other molecule with which it is ordinarily associated, for example, in its natural environment. An isolated nucleic acid molecule includes a nucleic acid molecule contained in cells that ordinarily express the nucleic acid molecule, but the nucleic acid molecule is present extrachromasomally or at a chromosomal location that is different from its natural chromosomal location.

% homology: The term "% homology" is used interchangeably herein with the term "% identity" herein and refers to the level of nucleic acid or amino acid sequence identity between the nucleic acid sequence that encodes any one of the inventive polypeptides or the inventive polypeptide's amino acid sequence, when aligned using a sequence alignment program.

For example, as used herein, 80% homology means the same thing as 80% sequence identity determined by a defined algorithm, and accordingly a homologue of a given sequence has greater than 80% sequence identity over a length of the given sequence. Exemplary levels of sequence identity include, but are not limited to, 80, 85, 90, 95, 98% or more sequence identity to a given sequence, e.g., the coding sequence for any one of the inventive polypeptides, as described herein.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet. See also, Altschul, et al., 1990 and Altschul, et al., 1997.

Sequence searches are typically carried out using the BLASTN program when evaluating a given nucleic acid sequence relative to nucleic acid sequences in the GenBank DNA Sequences and other public databases. The BLASTX program is preferred for searching nucleic acid sequences that have been translated in all reading frames against amino acid sequences in the GenBank Protein Sequences and other public databases. Both BLASTN and BLASTX are run using default parameters of an open gap penalty of 11.0, and an extended gap penalty of 1.0, and utilize the BLOSUM-62 matrix. (See, e.g., Altschul, S. F., et al., Nucleic Acids Res. 25:3389-3402, 1997.)

A preferred alignment of selected sequences in order to determine "% identity" between two or more sequences, is performed using for example, the CLUSTAL-W program in MacVector version 13.0.7, operated with default parameters, including an open gap penalty of 10.0, an extended gap penalty of 0.1, and a BLOSUM 30 similarity matrix.

Modified DNA polymerase: As used herein, the term "modified DNA polymerase" refers to a DNA polymerase originated from another (i.e., parental) DNA polymerase and contains one or more amino acid alterations (e.g., amino acid substitution, deletion, or insertion) compared to the parental DNA polymerase. In some embodiments, a modified DNA polymerases of the invention is originated or modified from a naturally-occurring or wild-type DNA polymerase. In some embodiments, a modified DNA polymerase of the invention is originated or modified from a recombinant or engineered DNA polymerase including, but not limited to, chimeric DNA polymerase, fusion DNA polymerase or another modified DNA polymerase. Typically, a modified DNA polymerase has at least one changed phenotype compared to the parental polymerase.

Mutation: As used herein, the term "mutation" refers to a change introduced into a parental sequence, including, but not limited to, substitutions, insertions, deletions (including truncations). The consequences of a mutation include, but are not limited to, the creation of a new character, property, function, phenotype or trait not found in the protein encoded by the parental sequence.

Mutant: As used herein, the term "mutant" refers to a modified protein which displays altered characteristics when compared to the parental protein. The terms "variant" and "mutant" are used interchangeably herein.

Wild-type: As used herein, the term "wild-type" refers to a gene or gene product which has the characteristics of that gene or gene product when isolated from a naturally-occurring source.

Fidelity: As used herein, the term "fidelity" refers to either the accuracy of DNA polymerization by template-dependent DNA polymerase or the measured difference in $k_{off}$ of the correct nucleotide vs incorrect nucleotide binding to the template DNA. The fidelity of a DNA polymerase is typically measured by the error rate (the frequency of incorporating an inaccurate nucleotide, i.e., a nucleotide that is not incorporated at a template-dependent manner). The accuracy or fidelity of DNA polymerization is maintained by both the polymerase activity and the 3'-5' exonuclease activity of a DNA polymerase. The term "high fidelity" refers to an error rate less than $4.45 \times 10^{-6}$ (e.g., less than $4.0 \times 10^{-6}$, $3.5 \times 10^{-6}$, $3.0 \times 10^{-6}$, $2.5 \times 10^{-6}$, $2.0 \times 10^{-6}$, $1.5 \times 10^{-6}$, $1.0 \times 10^{-6}$, $0.5 \times 10^{-6}$) mutations/nt/doubling. The fidelity or error rate of a DNA polymerase may be measured using assays known to the art. For example, the error rates of DNA polymerases can be tested as described herein or as described in Johnson, et al., Biochim Biophys Acta. 2010 May; 1804(5): 1041-1048.

Nanopore: The term "nanopore," as used herein, generally refers to a pore, channel or passage formed or otherwise provided in a membrane. A membrane may be an organic membrane, such as a lipid bilayer, or a synthetic membrane, such as a membrane formed of a polymeric material. The membrane may be a polymeric material. The nanopore may be disposed adjacent or in proximity to a sensing circuit or an electrode coupled to a sensing circuit, such as, for example, a complementary metal-oxide semiconductor (CMOS) or field effect transistor (FET) circuit. In some examples, a nanopore has a characteristic width or diameter on the order of 0.1 nanometers (nm) to about 1000 nm. Some nanopores are proteins. Alpha-hemolysin, MspA are examples of a protein nanopore.

Nucleotide: As used herein, a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide. A sequence of operatively linked nucleotides is typically referred to herein as a "base sequence" or "nucleotide sequence," and is represented herein by a formula whose left to right orientation is in the conventional direction of 5'-terminus to 3'-terminus. As used herein, a "modified nucleotide" refers to a polyphosphate, e.g., 3, 4, 5, 6, 7 or 8 phosphates, nucleotide.

Oligonucleotide or Polynucleotide: As used herein, the term "oligonucleotide" is defined as a molecule including two or more deoxyribonucleotides and/or ribonucleotides, preferably more than three. Its exact size will depend on many factors, which in turn depend on the ultimate function or use of the oligonucleotide. The oligonucleotide may be derived synthetically or by cloning. As used herein, the term "polynucleotide" refers to a polymer molecule composed of nucleotide monomers covalently bonded in a chain. DNA (deoxyribonucleic acid) and RNA (ribonucleic acid) are examples of polynucleotides.

Polymerase: As used herein, a "polymerase" refers to an enzyme that catalyzes the polymerization of nucleotide (i.e., the polymerase activity). Generally, the enzyme will initiate synthesis at the 3'-end of the primer annealed to a polynucleotide template sequence, and will proceed toward the 5' end of the template strand. A "DNA polymerase" catalyzes the polymerization of deoxynucleotides.

Primer: As used herein, the term "primer" refers to an oligonucleotide, whether occurring naturally or produced synthetically, which is capable of acting as a point of initiation of nucleic acid synthesis when placed under conditions in which synthesis of a primer extension product which is complementary to a nucleic acid strand is induced, e.g., in the presence of four different nucleotide triphosphates and thermostable enzyme in an appropriate buffer ("buffer" includes pH, ionic strength, cofactors, etc.) and at a suitable temperature. The primer is preferably single-stranded for maximum efficiency in amplification, but may alternatively be double-stranded. If double-stranded, the primer is first treated to separate its strands before being used to prepare extension products. Preferably, the primer is an oligodeoxyribonucleotide. The primer must be sufficiently long to prime the synthesis of extension products in the presence of the thermostable enzyme. The exact lengths of the primers will depend on many factors, including temperature, source of primer and use of the method. For example, depending on the complexity of the target sequence, the oligonucleotide primer typically contains 15-25 nucleotides, although it may contain more or few nucleotides. Short primer molecules generally require colder temperatures to form sufficiently stable hybrid complexes with template.

Processivity: As used herein, "processivity" refers to the ability of a polymerase to remain attached to the template and perform multiple modification reactions. "Modification reactions" include but are not limited to polymerization, and exonucleolytic cleavage. In some embodiments, "processivity" refers to the ability of a DNA polymerase to perform a sequence of polymerization steps without intervening dissociation of the enzyme from the growing DNA chains. Typically, "processivity" of a DNA polymerase is measured by the length of nucleotides (for example 20 nts, 300 nts, 0.5-1 kb, or more) that are polymerized or modified without intervening dissociation of the DNA polymerase from the growing DNA chain. "Processivity" can depend on the nature of the polymerase, the sequence of a DNA template, and reaction conditions, for example, salt concentration, temperature or the presence of specific proteins. As used herein, the term "high processivity" refers to a processivity higher than 20 nts (e.g., higher than 40 nts, 60 nts, 80 nts, 100 nts, 120 nts, 140 nts, 160 nts, 180 nts, 200 nts, 220 nts, 240 nts, 260 nts, 280 nts, 300 nts, 320 nts, 340 nts, 360 nts, 380 nts, 400 nts, or higher) per association/disassociation with the template. Processivity can be measured according the methods defined herein and in WO 01/92501 A1 (MJ Bioworks, Inc., Improved Nucleic Acid Modifying Enzymes, published 6 Dec. 2001).

Synthesis: As used herein, the term "synthesis" refers to any in vitro method for making new strand of polynucleotide or elongating existing polynucleotide (i.e., DNA or RNA) in a template dependent manner Synthesis, according to the invention, includes amplification, which increases the number of copies of a polynucleotide template sequence with the use of a polymerase. Polynucleotide synthesis (e.g., amplification) results in the incorporation of nucleotides into a polynucleotide (i.e., a primer), thereby forming a new polynucleotide molecule complementary to the polynucleotide template. The formed polynucleotide molecule and its template can be used as templates to synthesize additional polynucleotide molecules. "DNA synthesis," as used herein, includes, but is not limited to, PCR, the labeling of polynucleotide (i.e., for probes and oligonucleotide primers), polynucleotide sequencing.

Template DNA molecule: As used herein, the term "template DNA molecule" refers to a strand of a nucleic acid from which a complementary nucleic acid strand is synthesized by a DNA polymerase, for example, in a primer extension reaction.

Template-dependent manner: As used herein, the term "template-dependent manner" refers to a process that involves the template dependent extension of a primer molecule (e.g., DNA synthesis by DNA polymerase). The term "template-dependent manner" typically refers to polynucleotide synthesis of RNA or DNA wherein the sequence of the newly synthesized strand of polynucleotide is dictated by the well-known rules of complementary base pairing (see, for example, Watson, J. D. et al., In: Molecular Biology of the Gene, 4th Ed., W. A. Benjamin, Inc., Menlo Park, Calif. (1987)).

Tag: As used herein, the term "tag" refers to a detectable moiety that may be atoms or molecules, or a collection of atoms or molecules. A tag may provide an optical, electrochemical, magnetic, or electrostatic (e.g., inductive, capacitive) signature, which signature may be detected with the aid of a nanopore.

Tagged Nucleotide: As used herein, the term "tagged nucleotide" refers to a nucleotide or modified nucleotide that has a tag attached. The tag may be attached covalently to the sugar, the phosphate (or polyphosphate) or base. The tag may be on the terminal phosphate.

Vector: As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

The polymerase variants provided for herein are useful in the chip-based polynucleotide sequencing as described in WO2013/188841 (Genia Technologies, Inc., Chip Set-Up and High-Accuracy Nucleic Acid Sequencing, published 19 Dec. 2013).

Desired characteristics of a polymerase that finds use in sequencing DNA are:
  a. Slow $k_{off}$ (for modified nucleotide)
  b. Fast $k_{on}$ (for modified nucleotide)
  c. High fidelity
  d. Low exonuclease activity
  e. DNA strand displacement
  f. Faster $k_{chem}$ (for modified nucleotide substrates)
  g. Increased stability
  h. Processivity
  i. Salt tolerance
  j. Compatible with attachment to nanopore
  k. Ability to incorporate a polyphosphates having 4, 5, 6, 7 or 8 phosphates, e.g., quadraphosphate, pentaphosphate, hexaphosphate, heptaphosphate or octophosphate nucleotide
  l. Sequencing accuracy
  m. Long read lengths, i.e., long continuous reads.

Nomenclature

In the present description and claims, the conventional one-letter and three-letter codes for amino acid residues are used.

For ease of reference, polymerase variants of the application are described by use of the following nomenclature:

Original amino acid(s): position(s): substituted amino acid(s). According to this nomenclature, for instance the substitution of serine by an alanine in position 242 is shown as:
  Ser242Ala or S242A
  Multiple mutations are separated by plus signs, i.e.:
  Ala30Asp+Glu34Ser or A30N+E34S
representing mutations in positions 30 and 34 substituting alanine and glutamic acid for asparagine and serine, respectively.

When one or more alternative amino acid residues may be inserted in a given position it is indicated as: A30N/E or A30N or A30E.

Unless otherwise stated, the number of the residues corresponds to the residue numbering of SEQ ID NO:2.

Site-Directed Mutagenesis of Polymerase

Clostridium phage phiCPV4 wild type sequences are provided herein (SEQ ID NO:3, nucleic acid coding region plus a His-tag; SEQ ID NO:1, protein coding region) and available elsewhere (National Center for Bioinformatics or GenBank Accession Numbers AFH27113).

Point mutations may be introduced using QuikChange Lightning 2 kit (Stategene/Agilent) following manufacturer's instructions.

Primers can be ordered from commercial companies, e.g., IDT DNA.

Nanopore Assembly and Insertion

The methods described herein can use a nanopore having a polymerase attached to the nanopore. In some cases, it is desirable to have one and only one polymerase per nanopore (e.g., so that only one nucleic acid molecule is sequenced at each nanopore). However, many nanopores, including, e.g., alpha-hemolysin (aHL), can be multimeric proteins having a plurality of subunits (e.g., 7 subunits for aHL). The subunits can be identical copies of the same polypeptide. Provided herein are multimeric proteins (e.g., nanopores) having a defined ratio of modified subunits (e.g., a-HL variants) to un-modified subunits (e.g., a-HL). Also provided herein are methods for producing multimeric proteins (e.g., nanopores) having a defined ratio of modified subunits to un-modified subunits.

With reference to FIG. 27 of WO2014/074727 (Genia Technologies, Inc.), a method for assembling a protein having a plurality of subunits comprises providing a plurality of first subunits 2705 and providing a plurality of second subunits 2710, where the second subunits are modified when compared with the first subunits. In some cases, the first subunits are wild-type (e.g., purified from native sources or produced recombinantly). The second subunits can be modified in any suitable way. In some cases, the second subunits have a protein (e.g., a polymerase) attached (e.g., as a fusion protein).

The modified subunits can comprise a chemically reactive moiety (e.g., an azide or an alkyne group suitable for forming a linkage). In some cases, the method further comprises performing a reaction (e.g., a Click chemistry cycloaddition) to attach an entity (e.g., a polymerase) to the chemically reactive moiety.

The method can further comprise contacting the first subunits with the second subunits 2715 in a first ratio to form a plurality of proteins 2720 having the first subunits and the second subunits. For example, one part modified aHL subunits having a reactive group suitable for attaching a polymerase can be mixed with six parts wild-type aHL subunits (i.e., with the first ratio being 1:6). The plurality of proteins can have a plurality of ratios of the first subunits to the second subunits. For example, the mixed subunits can form several nanopores having a distribution of stoichiometries of modified to un-modified subunits (e.g., 1:6, 2:5, 3:4).

In some cases, the proteins are formed by simply mixing the subunits. In the case of aHL nanopores for example, a detergent (e.g., deoxycholic acid) can trigger the aHL monomer to adopt the pore conformation. The nanopores can also be formed using a lipid (e.g., 1,2-diphytanoyl-sn-glycero-3-phosphocholine (DPhPC) or 1,2-di-O-phytanyl-sn-glycero-3-phosphocholine (DoPhPC)) and moderate temperature (e.g., less than about 100° C.). In some cases, mixing DPhPC with a buffer solution creates large multi-lamellar vesicles (LMV), and adding aHL subunits to this solution and incubating the mixture at 40° C. for 30 minutes results in pore formation.

If two different types of subunits are used (e.g., the natural wild type protein and a second aHL monomer which can contain a single point mutation), the resulting proteins can have a mixed stoichiometry (e.g., of the wild type and mutant proteins). The stoichiometry of these proteins can follow a formula which is dependent upon the ratio of the concentrations of the two proteins used in the pore forming reaction. This formula is as follows:

$$100 P_m = 100[n!/m!(n-m)!] \cdot f_{mut}^m \cdot f_{wt}^{n-m}, \text{ where}$$

$P_m$=probability of a pore having m number of mutant subunits
n=total number of subunits (e.g., 7 for aHL)
m=number of "mutant" subunits
$f_{mut}$=fraction or ratio of mutant subunits mixed together
$f_{wt}$=fraction or ratio of wild-type subunits mixed together The method can further comprise fractionating the plurality of proteins to enrich proteins that have a second ratio of the first subunits to the second subunits 2725. For example, nanopore proteins can be isolated that have one and only one modified subunit (e.g., a second ratio of 1:6). However, any second ratio is suitable. A distribution of second ratios can also be fractionated such as enriching proteins that have either one or two modified subunits. The total number of subunits forming the protein is not always 7 (e.g., a different nanopore can be used or an alpha-hemolysin nanopore can form having six subunits) as depicted in FIG. 27 of WO2014/074727. In some cases, proteins having only one modified subunit are enriched. In such cases, the second ratio is 1 second subunit per (n−1) first subunits where n is the number of subunits comprising the protein.

The first ratio can be the same as the second ratio, however this is not required. In some cases, proteins having mutated monomers can form less efficiently than those not having mutated subunits. If this is the case, the first ratio can be greater than the second ratio (e.g., if a second ratio of 1 mutated to 6 non-mutated subunits are desired in a nanopore, forming a suitable number of 1:6 proteins may require mixing the subunits at a ratio greater than 1:6).

Proteins having different second ratios of subunits can behave differently (e.g., have different retention times) in a separation. In some cases, the proteins are fractionated using chromatography, such as ion exchange chromatography or affinity chromatography. Since the first and second subunits can be identical apart from the modification, the number of modifications on the protein can serve as a basis for separation. In some cases, either the first or second subunits have a purification tag (e.g., in addition to the modification) to allow or improve the efficiency of the fractionation. In some cases, a poly-histidine tag (His-tag), a streptavidin tag (Strep-tag), or other peptide tag is used. In some instances, the first and second subunits each comprise different tags and the fractionation step fractionates on the basis of each tag. In the case of a His-tag, a charge is created on the tag at low pH (Histidine residues become positively charged below the pKa of the side chain). With a significant difference in charge on one of the aHL molecules compared to the others, ion exchange chromatography can be used to separate the oligomers which have 0, 1, 2, 3, 4, 5, 6, or 7 of the "charge-tagged" aHL subunits. In principle, this charge tag can be a string of any amino acids which carry a uniform charge. FIGS. 28 and 29 of WO2014/074727 show examples of fractionation of nanopores based on a His-tag. FIG. 28 WO2014/074727 shows a plot of ultraviolet absorbance at 280 nanometers, ultraviolet absorbance at 260 nanometers, and conductivity. The peaks correspond to nanopores with various ratios of modified and unmodified subunits. FIG. 29 of WO2014/074727 shows fractionation of aHL nanopores and mutants thereof using both His-tag and Strep-tags.

In some cases, an entity (e.g., a polymerase) is attached to the protein following fractionation. The protein can be a nanopore and the entity can be a polymerase. In some instances, the method further comprises inserting the proteins having the second ratio subunits into a bilayer.

In some situations, a nanopore can comprise a plurality of subunits. A polymerase can be attached to one of the subunits and at least one and less than all of the subunits comprise a first purification tag. In some examples, the nanopore is alpha-hemolysin or a variant thereof. In some instances, all of the subunits comprise a first purification tag or a second purification tag. The first purification tag can be a poly-histidine tag (e.g., on the subunit having the polymerase attached).

Polymerase attached to Nanopore

In some cases, a polymerase (e.g., DNA polymerase) is attached to and/or is located in proximity to the nanopore. The polymerase can be attached to the nanopore before or after the nanopore is incorporated into the membrane. In some instances, the nanopore and polymerase are a fusion protein (i.e., single polypeptide chain).

The polymerase can be attached to the nanopore in any suitable way. In some cases, the polymerase is attached to the nanopore (e.g., hemolysin) protein monomer and then the full nanopore heptamer is assembled (e.g., in a ratio of one monomer with an attached polymerase to 6 nanopore (e.g., hemolysin) monomers without an attached polymerase). The nanopore heptamer can then be inserted into the membrane.

Another method for attaching a polymerase to a nanopore involves attaching a linker molecule to a hemolysin monomer or mutating a hemolysin monomer to have an attachment site and then assembling the full nanopore heptamer (e.g., at a ratio of one monomer with linker and/or attachment site to 6 hemolysin monomers with no linker and/or attachment site). A polymerase can then be attached to the attachment site or attachment linker (e.g., in bulk, before inserting into the membrane). The polymerase can also be attached to the attachment site or attachment linker after the (e.g., heptamer) nanopore is formed in the membrane. In some cases, a plurality of nanopore-polymerase pairs are inserted into a plurality of membranes (e.g., disposed over the wells and/or electrodes) of the biochip. In some instances, the attachment of the polymerase to the nanopore complex occurs on the biochip above each electrode.

The polymerase can be attached to the nanopore with any suitable chemistry (e.g., covalent bond and/or linker). In some cases, the polymerase is attached to the nanopore with molecular staples. In some instances, molecular staples comprise three amino acid sequences (denoted linkers A, B and C). Linker A can extend from a hemolysin monomer, Linker B can extend from the polymerase, and Linker C then can bind Linkers A and B (e.g., by wrapping around both Linkers A and B) and thus the polymerase to the nanopore. Linker C can also be constructed to be part of Linker A or Linker B, thus reducing the number of linker molecules.

In some instances, the polymerase is linked to the nanopore using Solulink™ chemistry. Solulink™ can be a reaction between HyNic (6-hydrazino-nicotinic acid, an aromatic hydrazine) and 4FB (4-formylbenzoate, an aromatic aldehyde). In some instances, the polymerase is linked to the nanopore using Click chemistry (available from LifeTechnologies for example). In some cases, zinc finger mutations are introduced into the hemolysin molecule and then a molecule is used (e.g., a DNA intermediate molecule) to link the polymerase to the zinc finger sites on the hemolysin.

Other linkers that may find use in attaching the polymerase to a nanopore are direct genetic linkage (e.g., $(GGGGS)_{1-3}$ (SEQ ID NO: 4) amino acid linker), transglutaminase mediated linking (e.g., RSKLG (SEQ ID NO: 5)), sortase mediated linking, and chemical linking through cysteine modifications. Specific linkers contemplated as useful herein are $(GGGGS)_{1-3}$ (SEQ ID NO: 4), K-tag (RSKLG(SEQ ID NO: 5)) on N-terminus, ΔTEV site (12-25), ΔTEV site+N-terminus of SpyCatcher (12-49).

Apparatus Set-Up

The nanopore may be formed or otherwise embedded in a membrane disposed adjacent to a sensing electrode of a sensing circuit, such as an integrated circuit. The integrated circuit may be an application specific integrated circuit (ASIC). In some examples, the integrated circuit is a field effect transistor or a complementary metal-oxide semiconductor (CMOS). The sensing circuit may be situated in a chip or other device having the nanopore, or off of the chip or device, such as in an off-chip configuration. The semiconductor can be any semiconductor, including, without limitation, Group IV (e.g., silicon) and Group III-V semiconductors (e.g., gallium arsenide). See, for example, WO 2013/123450, for the apparatus and device set-up for sensing a nucleotide or tag.

Pore based sensors (e.g., biochips) can be used for electro-interrogation of single molecules. A pore based sensor can include a nanopore of the present disclosure formed in a membrane that is disposed adjacent or in proximity to a sensing electrode. The sensor can include a counter electrode. The membrane includes a trans side (i.e., side facing the sensing electrode) and a cis side (i.e., side facing the counter electrode).

In the experimental disclosure which follows, the following abbreviations apply: eq (equivalents); M (Molar); µM (micromolar); N (Normal); mol (moles); mmol (millimoles); µmol (micromoles); nmol (nanomoles); g (grams); mg (milligrams); kg (kilograms); µg (micrograms); L (liters); ml (milliliters); µl (microliters); cm (centimeters); mm (millimeters); µm (micrometers); nm (nanometers); ° C. (degrees Centigrade); h (hours); min (minutes); sec (seconds); msec (milliseconds).

EXAMPLES

The present invention is described in further explained in the following examples which are not in any way intended to limit the scope of the invention as claimed. The attached Figures are meant to be considered as integral parts of the specification and description of the invention. All references cited are herein specifically incorporated by reference for all that is described therein. The following examples are offered to illustrate, but not to limit the claimed invention.

Example 1

Directed Mutagenesis

This example illustrates the introduction of a mutation into a pol6 polymerase at a desired position.

DNA encoding the His-tagged wild-type pol6 was purchased from a commercial source (DNA 2.0, Menlo Park, Calif.). The sequence was verified by sequencing.

For the mutant screen, we expressed the polymerase as is (N-ter His-Pol6). In order to test the pol hits on the chip, we engineered in a SpyCatcher domain in N-ter or C-ter of Pol6.

Rational positions to impact Pol6-nucleotide binding were identified based on homology modeling of known crystal structures.

For the primary screen, each of the rational positions were mutated into Gly, Ala, Leu, Glu, Gln, Lys, His, Tyr, Pro, Trp, Thr or Met using the Q5 mutagenesis protocol.

The primers for each mutagenesis reaction was designed using the NEB base changer protocol and ordered in 96-well plate format from IDT.

The forward and reverse primers were 5' phosphorylated in high throughput (HTP) format using the T4 polynucleotidekinase (PNK) purchased from NEB. A typical 25-µl reaction contained 15 µl of primer at 10 µM, 5 µl of 5× reaction buffer (from NEB), 1.25 µl PNK enzyme, 3.75 µl water. The reaction was performed at 37° C. for 30 min and the enzyme heat inactivated at 65° C. for 20 min.

PCR mutagenesis was performed using Q5 DNA polymerase from NEB. A typical 25 µl reaction contained 5 µl of Q5 buffer, 5 µl of GC enhancer, 0.5 µl of 10 mM dNTPs, 1.25 µl of 10 µM phosphorylated mutagenesis primers forward and reverse, 0.25 µl Q5 polymerase and 1 µl of 5 ng/ml wild type Pol6 template, i.e., His-Pol6, and 10.75 µl $H_2O$.

Once PCR is complete, 0.5 µl of Dpn1 was added to 25 µl PCR mix and incubated at 37° C. for 1 hr.

Add 2.5 µl of Dpn1 treated PCR product with 2.5 µl of Blunt/TA ligase master mix. Incubate at room temperature for 1 hr.

Add 1 µl of ligation mix to 20 µl of 96-well BL21 DE3 cells (EMD Millipore) and incubate on ice for 5 min.

Heat shock at 42° C. for exactly 30 sec using the PCR device and place on ice for 2 min.

Add 80 µl of SOC and incubate at 37° C. incubator for 1 hr without shaking.

Add 100 µl of SOC or ultra pure water and plate them in 48-well LB-agar plates with 50-100 µg/ml kanamycin.

Example 2

Expression and Purification

The following example details how the pol6 variants were expressed and purified using a high throughput method.

DNA encoding the variants in the pD441 vector (expression plasmid) was transformed into competent *E. coli* and glycerol stocks made. Starting from a tiny pick of the glycerol stock, grow 1 ml starter culture in LB with 0.2% Glucose and 100 µg/ml Kanamycin for approximately 8 hrs. Transfer 25 µl of log phase starter culture into 1 ml of expression media (Terrific Broth (TB) autoinduction media supplemented with 0.2% glucose, 50 mM Potassium Phosphate, 5 mM MgCl2 and 100 µg/ml Kanamycin) in 96-deep well plates. The plates were incubated with shaking at 250-300 rpm for 36-40 hrs at 28° C.

Cells were then harvested via centrifugation at 3200×g for 30 minutes at 4° C. The media was decanted off and the cell pellet resuspended in 200 µl pre-chilled lysis buffer (20 mM Potassium Phosphate pH 7.5, 100 mM NaCl, 0.5% Tween20, 5 mM TCEP, 10 mM Imidazole, 1 mM PMSF, 1× Bug Buster, 100 µg/ml Lysozyme and protease inhibitors) and incubate at room temperature for 20 min with mild agitation. Then add 20 µl from a 10× stock to a final concentration of 100 µg/ml DNase, 5 mM MgCl2, 100 µg/ml RNase I and incubate in on ice for 5-10 min to produce a lysate. Supplement the lysate with 200 µl of 1M Potassium Phosphate, pH 7.5 (Final concentration will be about 0.5M Potassium phosphate in 400 µl lysate) and filter through Pall filter plates (Part #5053, 3 micron filters) via centrifugation at approximately 1500 rpm at 4 C for 10 minutes. The clarified lysates were then applied to equilibrated 96-well His-Pur Cobalt plates (Pierce Part #90095) and bind for 15-30 min.

The flow through (FT) was collected by centrifugation at 500×G for 3 min. The FT was then washed 3 times with 400 µl of wash buffer 1 (0.5M Potassium Phosphate pH 7.5, 1M NaCl 5 mM TCEP, 20 mM Imidazole+0.5% Tween20). The FT was then washed twice in 400 ul wash buffer 2 (50 mM Tris pH 7.4, 200 mM KCl, 5 mM TCEP, 0.5% Tween20, 20 mM Imidazole).

The Pol6 was eluted using 200 µl elution buffer (50 mM Tris Ph7.4, 200 mM KCl, 5 mM TCEP, 0.5% Tween20, 300 mM Imidazole, 25% Glycerol) and collected after 1-2 min incubation. Reapply eluate to the same His-Pur plate2-3 times to get concentrated Pol6 in elute. The purified polymerase is >95% pure as evaluated by SDS-PAGE. The protein concentration is ~3 uM (0.35 mg/ml) with a 260/280 ratio of 0.6 as evaluated by Nanodrop.

Polymerase activity is checked by Fluorescence displacement assay (see Example 3).

Example 3

Determination of Activity

This example provides methods of determining the activity of the variant polymerases.

Displacement Assay Protocol

This assay characterizes the mutant polymerase's ability to incorporate polyphosphate nucleotides into a DNA strand as well as its ability to unwind and displace double-stranded DNA.

Stock reagents are as follows:

Low Salt

| Reagent | Reagent A Concentration | Reagent B Concentration |
|---|---|---|
| KCl | 21.4 mM | 20 mM |
| Bicine 7.9 | 26.75 mM | 25 mM |
| EDTA | 0.284 mM | N/A |
| Triton X-100 | 0.0535 % | 0.05 % |
| DTT | 5.35 mM | 5 mM |
| BSA | 26.75 µg/ml | 25 µg/ml |
| DNA FRET Template | 71 nM | N/A |
| MgSO4 | N/A | 20 mM |

N/A = not applicable

High Salt

| Reagent | Reagent A Concentration | Reagent B Concentration |
|---|---|---|
| NaCl | 75 mM | 300 or 150 mM |
| HEPES 7.5 | 32.6 mM | 25 mM |
| EDTA | 0.3 mM | N/A |
| Triton X-100 | 0.065 % | 0.05 % |
| TCEP | 6.5 mM | 5 mM |
| BSA | 32.6 µg/ml | 25 µg/ml |
| DNA FRET Template | 87 nM | N/A |
| MgCl | N/A | 20 mM |

N/A = not applicable

For screening single and double mutants:

Using Reagent A as diluent, make 4 different nucleotide conditions at 1.42×:

1

| Nucleotide | [1.42X] | [Final] |
|---|---|---|
| dTnP-NH2 | 28.4 µM | 20 µM |
| dATP | 21.3 µM | 15 µM |
| dCTP | 21.3 µM | 15 µM |
| dGTP | 21.3 µM | 15 µM |

2

| Nucleotide | [1.42X] | [Final] |
|---|---|---|
| dTnP-NH2 | 2.84 µM | 2 µM |
| dATP | 21.3 µM | 15 µM |
| dCTP | 21.3 µM | 15 µM |
| dGTP | 21.3 µM | 15 µM |

4

| Nucleotide | [1.42X] | [Final] |
|---|---|---|
| dTnP-NH2 | 0 | 0 |
| dATP | 0 | 0 |
| dCTP | 0 | 0 |
| dGTP | 0 | 0 |

3

| Nucleotide | [1.42X] | [Final] |
|---|---|---|
| dTnP-NH2 | 0 µM | 0 µM |
| dATP | 21.3 µM | 15 µM |
| dCTP | 21.3 µM | 15 µM |
| dGTP | 21.3 µM | 15 µM |

For screening triple mutants:

Using Reagent A as diluent, make 4 different nucleotide conditions at 1.42×:

1

| Nucleotide | [1.42X] | [Final] |
|---|---|---|
| dTnP-NH2 | 28.4 µM | 20 µM |
| dAnP-NH2 | 28.4 µM | 20 µM |
| dCnP-NH2 | 28.4 µM | 20 µM |
| dGnP-NH2 | 28.4 µM | 20 µM |

2

| Nucleotide | [1.42X] | [Final] |
|---|---|---|
| dTnP-NH2 | 1.42 µM | 1 µM |
| dAnP-NH2 | 1.42 µM | 1 µM |
| dCnP-NH2 | 1.42 µM | 1 µM |
| dGnP-NH2 | 1.42 µM | 1 µM |

4

| Nucleotide | [1.42X] | [Final] |
|---|---|---|
| dTnP-NH2 | 0 | 0 |
| dAnP-NH2 | 0 | 0 |
| dCnP-NH2 | 0 | 0 |
| dGnP-NH2 | 0 | 0 |

| 3 | | |
|---|---|---|
| Nucleotide | [1.42X] | [Final] |
| dTnP-NH2 | 0 μM | 0 μM |
| dATP | 21.3 μM | 15 μM |
| dCTP | 21.3 μM | 15 μM |
| dGTP | 21.3 μM | 15 μM | dNnP is a polyphosphate nucleotide where N is the nucleotide (i.e., A, T, C or G) and nP is 4-8 phosphates Nucleotide condition 1 tests for activity at high concentration of the hexaphosphate.

Nucleotide condition 2 tests for activity at low concentration of the hexaphosphate.

Nucleotide condition 3 tests for misincorporation rate (i.e., fidelity). If a mutant polymerase shows significant activity with only 3 of the 4 necessary nucleotides, then we conclude that it does not discriminate between correct or incorrect nucleotides while extending a DNA strand.

Nucleotide condition 4 tests for exonuclease activity. If a polymerase shows significant activity with no nucleotides present, then we conclude the polymerase is exhibiting exonuclease activity.

To each reaction well in a 96 well half-area transparent plate, add:

23 μl Reagent A/nucleotide mix

2 μl polymerase (1-10 μM)

Shake at 800 RPM on plate shaker for ~10 min.

Add 5 μl 1.4 M NaCl to each well to bring the NaCl concentration up to 300 mM or 5 μl 525 mM NaCl to each well to bring the NaCl concentration up to 150 mM.

Incubate for 30 minutes.

In BMG LABTECH plate reader, inject 10 μl reagent B and read fluorescence signal for 2 to 10 min.

Figure 5:
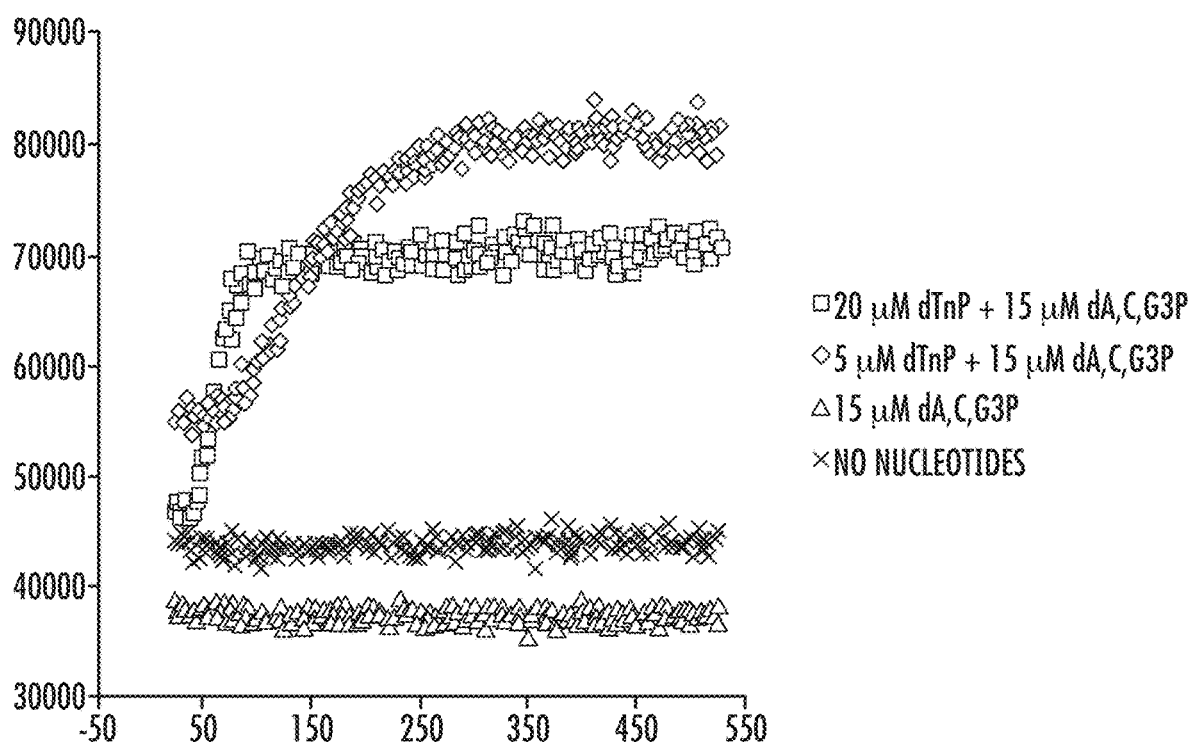
FIG. 5 is a graph showing representative data from the displacement assay for a variant polymerase. Reference is made to Example 3.

Representative data from the displacement assay for a variant polymerase are shown in FIG. 5. The activity of polymerase was measured using the displacement assay in the presence of A. 20 μM dTnP+15 μM dA,C,G3P (red squares; ■) B. 5 μM dTnP+15 μM dA,C,G3P (blue diamonds; ♦), C. 15 μM dA,C,G3P (green triangles; ▲), or D. in the absence of nucleotides (purple X's). A and B show that a mutant variant is able to incorporate and extend along a DNA template with a polyphosphate nucleotide. C shows that the variant has not lost its fidelity and is not misincorporating random nucleotides in the absence of a T nucleotide. D. shows that the signal generated is not a result of the polymerase exonuclease activity in the absence of all nucleotides. All four curves are representative of a single variant tested across 4 different assay plates as part of polymerase screen.

Example 4

Determination of $K_{OFF}$

The following stopped flow assay was used to determine the $k_{off}$ rate of the variant polymerases.

For reagent A, polymerase is bound to a fluorescein labeled DNA template-primer with a Cy3 (or Alexa555)-linked polyphosphate nucleotide in the presence of a non-catalytic divalent metal like Ca2+. This forms a FRET pair, fluorescein being the donor fluorophore and Cy3 being the acceptor fluorophore. Reagent B contains the chase nucleotide. For purposes of this assay, the first nucleotide to be incorporated into the template/primer is Cytosine.

Reagent A (75 mM NaCl, 25 mM HEPES (pH 7.5), 2 mM CaCl2, 250 nM Fluorescein-Template/Primer, 20 uM dCnP-Cy3, and >250 nM Polymerase) was freshly prepared by mixing the components ensuring that the polymerase is added last. Allow the polymerase to incubate in Reagent A for 10 minutes.

Reagent B (75 mM NaCl, 25 mM HEPES (pH 7.5), 2 mM CaCl2, and 200 uM dCTP) was prepared.

When reagent A and B are mixed, dCTP competes with dCnP-Cy3 for association, an increase in fluorescence is observed given the dCTP concentration is in excess. The assay can be performed with either a stop flow device (Kintek Corp) or a fluorescent plate reader. The increase in fluorescence versus time was fit to a first order or second order exponential to provide the kinetic constant $k_{off}$ for that particular polymerase.

The purification yields and $k_{off}$s for selected variants are presented in Table 1.

TABLE 1

Purification yields and koffs for select Po16 variants

| | $k_{off}$ (s$^{-1}$) | Yield from 2.5 ml prep (μg) |
|---|---|---|
| Good kon hit and moderately good activity at 20 uM | | |
| S366A + N535L + A547M | 0.0039 | 77.58 |
| Hits from 20 m0d (Good activity at 20 uM hexaphosphate nucleotide & very low or no activity at 0 uM) | | |
| T651Y + P542E + N545K | 0.0562 | 5.16 |
| T651Y + P542E + Q546W | 0.0201 | 64.58 |
| S366A + P542E + N545K | 0.0295 | 125.24 |
| Hits from 20MSR(Good activity at 20 uM, activity at 0 uM) | | |
| S366A + P542E + I652Q | 0.0440 | 196.63 |
| T651Y + P542E + S366A | 0.0583 | 10.11 |
| Hits from 1MSR/1Mod and also show moderately good activity at 20 uM | | |
| S366A + N535L + N545K | 0.0103 | 60.25 |
| T651Y + N535L + N545K | 0.0273 | 210.66 |
| S366A + N535L + T529M | 0.0327 | 153.09 |
| S366A + N535L + I652Q | 0.0097 | 161.55 |
| Double mutant hit | | |
| T651Y + N535L | 0.0312 | 281.84 |
| S366A + N535L | 0.0134 | 666.95 |

FP = Fluorescent polarization

Figure 10:
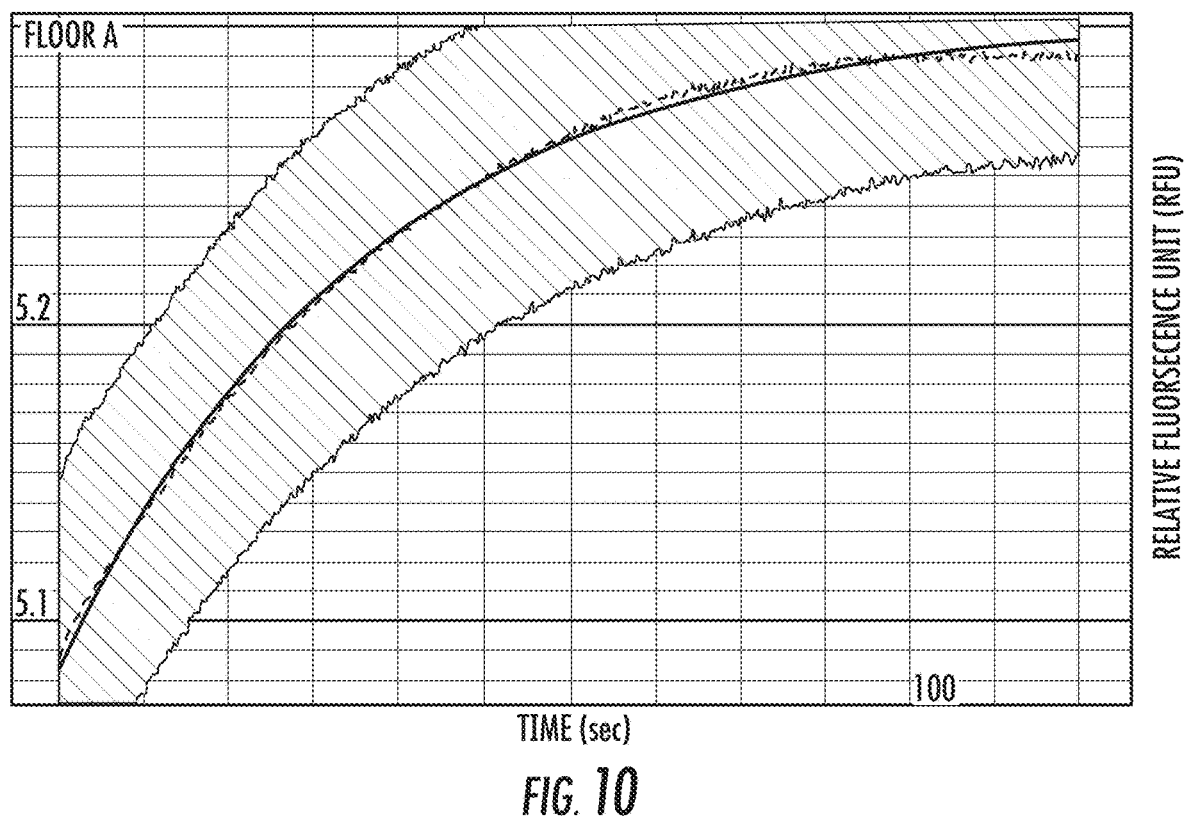
FIG. 10 is a graph of representative data from a fluorescence quenching based $k_{off}$ assay (see FIG. 3) for a variant polymerases. Preformed ternary complex of polymerase, Fluorescein-DNA template and dCnP-Alexa555 was preincubated in the presence of $Ca^{2+}$ and chased with excess native dCTP. Fluorescein fluorescence was monitored over time. $k_{off}$ measured from this is 0.028 s-1. The x-axis is time (T) in seconds and the y-axis is relative fluorescence units (RFU).

See FIG. 3 for a schematic representation of the assay and a graph of an exemplary reaction. See FIG. 10 for representative data.

Example 5

Determination of $K_{OFF}$

This example provides an alternative method using fluorescence polarization for determining the $k_{off}$.

An assay buffer comprising 25 mM Tris pH7.0, 75 mM KCl, 0.01% Triton-X100, 1× BSA (100 μg/ml), 0.5 mM EDTA, 2 mM CaCl2, 2 mM DTT, was used to prepare an assay master mix containing 250 nM hairpin fluorescein-labeled DNA template and 250 nM dC6P-C6-Cy3 tagged nucleotide. Fifty five microliters of the master mix were added to each of the wells of a black 96-well costar plate; and. 20 μl of polymerase mutants, which had been purified from 1 ml cultures, were added in a high throughput (HTP) format. The plate was shaken on a plate shaker for 1 minute to allow for the formation of homogenous ternary complexes of polymerase-DNA template-nucleotide. The plate was placed in a BMG polarstar plate reader (BMG LABTECH Inc., North Carolina) and target millipolarization was adjusted to 200 mP and 10% to have a gain around 2000. The excitation filter was set to 485 nM and the emission filter was set to 590-20 nM. The injector was primed with 1 ml of 1 mM dCTP chaser nucleotide solution. Data was collected with minimum 30 flashes per well per interval and 60 sec total read time for the start. The flashes were increased to 50 or higher and longer read times taken for the hit mutants that showed slow dissociation. Data collection began with the injection of 25 µl of 1 mM dCTP.

Figure 4:
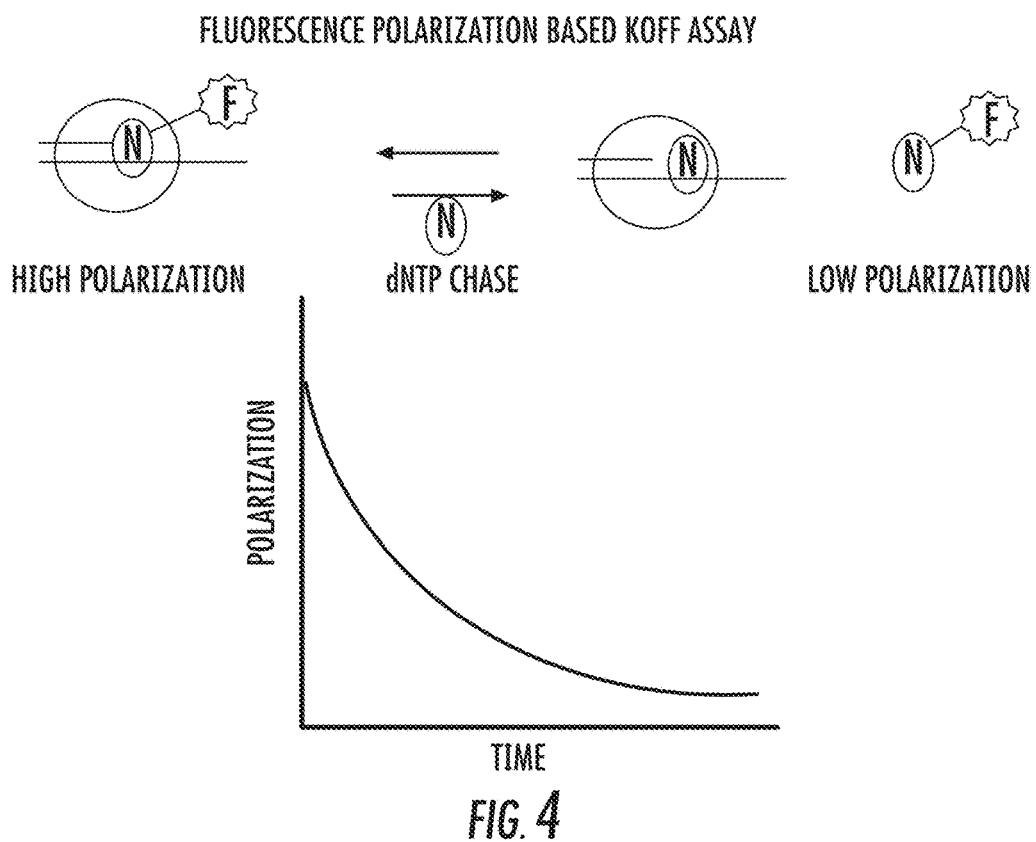
FIG. 4 is a depiction of the $k_{off}$ assay based on fluorescence polarization and an exemplary data trace. Reference is made to Example 5.

See FIG. 4 for a schematic representation of the assay and a graph of an exemplary reaction.

Figure 6:
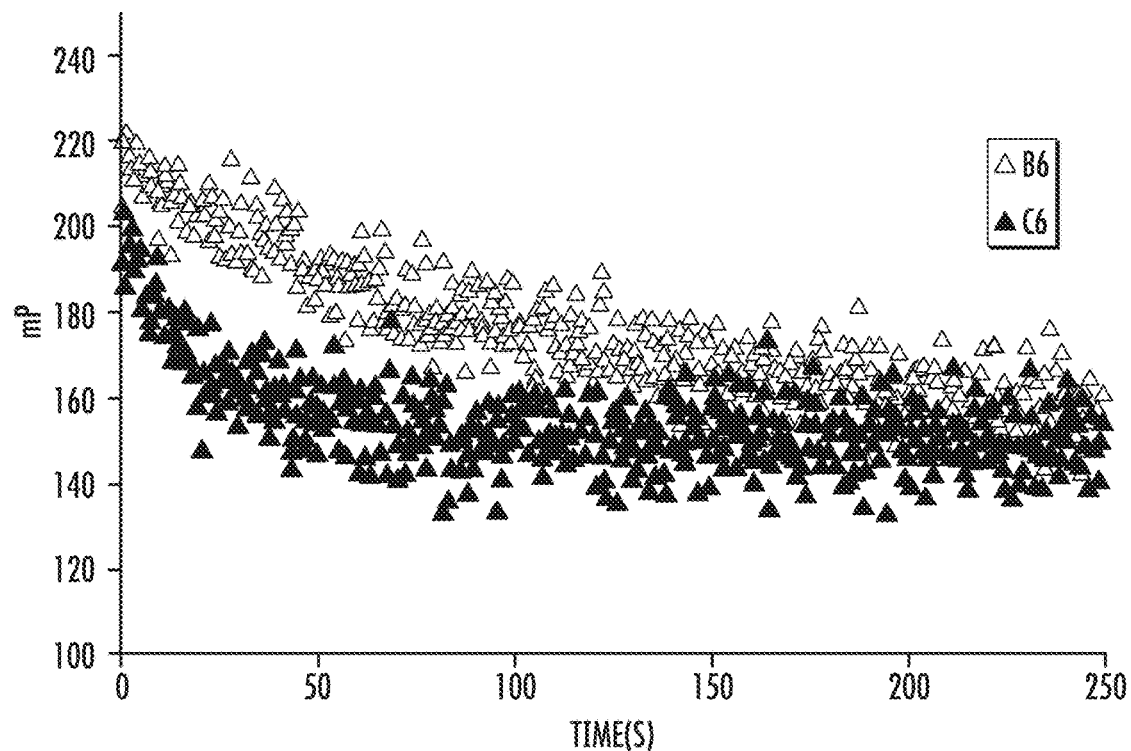
FIG. 6 is a graph of representative data from fluorescence polarization based $k_{off}$ assay for two variant polymerases. Reference is made to Example 5.

See FIG. 6 for representative data from fluorescence polarization based $k_{off}$ assay for two variant polymerases (S366A+N535L+I652Q (B6) and S366A+P542E+I652Q (C6)). mP is millipolarization. Preformed ternary complex of polymerase-DNA template –dCnP-Alexa555 is chased with native dCTP and polarization dCnP-Alexa555 was monitored over time.

Example 6

Determination of $K_{CHEM}$

This example provides a FRET based assay for determining the $k_{chem}$ for variant polymerases.

For reagent A, polymerase is bound to fluorescein labeled DNA template-primer. Reagent B contains Cy3 (or Alexa555)-linked polyphosphate nucleotide in the presence of a catalytic divalent metal like $Mg^{2+}$. For purposes of this protocol, the first nucleotide to be incorporated into the template/primer is Cytosine.

Reagent A (75 mM NaCl, 25 mM HEPES (pH 7.5), 250 nM Fluorescein-Template/Primer, >250 nM Polymerase) was prepared. The polymerase was allowed to incubate in Reagent A for 10 min.

Reagent B (75 mM NaCl, 25 mM HEPES (pH 7.5), 10 mM $MgCl_2$, and 20 uM dCnP-Cy3) was prepared.

When Reagent A and B are mixed, polymerase-fluorescein-template-primer complex binds dCnP-Cy3 and quenches fluorescence. $Mg^{2+}$ enables the polymerase to incorporate the nucleotide, which releases the cleavage product, pyrophosphate with attached Cy3, nP-Cy3. Since the quencher is released, fluorescence increases. The assay can be performed with either a stop flow device (Kintek Corp) or a fluorescent plate reader.

Figure 9:
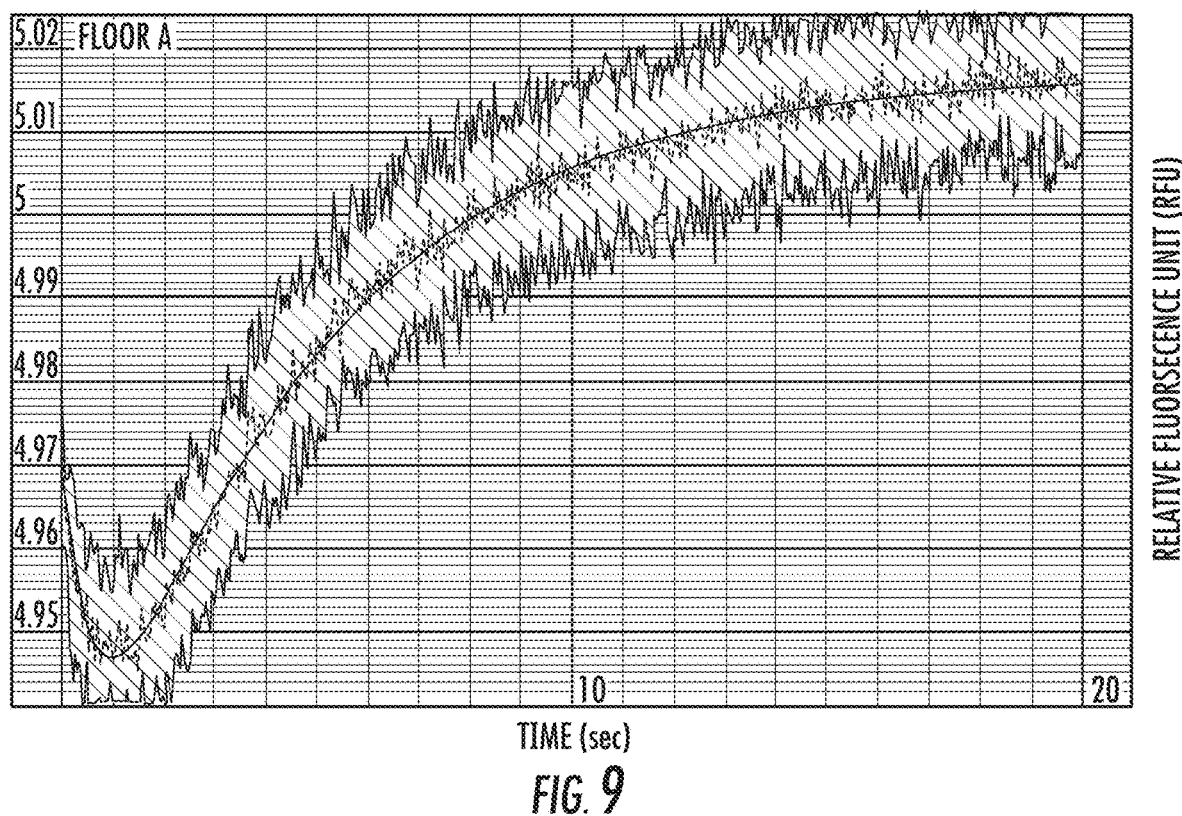
FIG. 9 is a graph of representative data from a fluorescence quenching based $k_{chem}$ assay (see FIG. 2) for a variant polymerase. Preformed binary complex of polymerase and Fluorescein-DNA template is mixed rapidly with saturating concentration of dCnP-Alexa555 in the presence of $Mg^{2+}$ using a Kintek stopped flow device. Fluorescein fluorescence is monitored over time. $k_{chem}$ estimated from the rate limiting step is 0.2 s-1. The x-axis is time (T) in seconds and the y-axis is relative fluorescence units (RFU).

See FIG. 2 for a schematic representation of the assay and a graph of an exemplary reaction. See FIG. 9 for representative data.

Example 7

Attachment to Nanopore

This example provides methods of attaching a variant polymerase to a nanopore, e.g., α-hemolysin.

The polymerase may be coupled to the nanopore by any suitable means. See, for example, PCT/US2013/068967 (published as WO2014/074727; Genia Technologies, Inc.), PCT/US2005/009702 (published as WO2006/028508; President and Fellows of Harvard College), and PCT/US2011/065640 (published as WO2012/083249; Columbia University).

The polymerase, e.g., a variant pol6 DNA Polymerase, was coupled to a protein nanopore (e.g. alpha-hemolysin), through a linker molecule. Specifically, the SpyTag and SpyCatcher system, that spontaneously forms covalent isopeptide linkages under physiological conditions was used. See, for example, Li et al, J Mol Biol. 2014 Jan. 23; 426(2):309-17.

The pol6 variant SpyCatcher HisTag was expressed according to Example 2 and purified using a cobalt affinity column. The SpyCatcher polymerase and the SpyTag oligomerized nanopore protein were incubated overnight at 4° C. in 3 mM $SrCl_2$. The 1:6-polymerase-template complex was then purified using size-exclusion chromatography.

The linker was attached at either the N-terminal or C-terminal of the pol6 variant. The N-terminally attached variants were found to be more robust, e.g., more stable. Therefore, N-terminally attached linkers were used.

Example 8

Activity on a Biochip

This example demonstrates the ability of a nanopore-bound variant polymerase to bind tagged nucleotides and thereby allow for the detection of blocked channel currents at the nanopore to which the polymerase is attached.

The polymerase was attached to a nanopore and embedded in a lipid bilayer over a well on a semiconductor sensor chip, also called a biochip. The lipid bilayer was formed and the nanopore with attached polymerase was inserted as described in PCT/US2014/061853 (entitled "Methods for Forming Lipid Bilayers on Biochips" and filed 22 Oct. 2014).

Variant polymerases were complexed with template DNA under low salt conditions.

The capability of the nanopore bound-variant polymerase to bind tagged nucleotides was determined in static capture experiments whereby tagged nucleotides are bound by the polymerase, and blocked channel current is measured as the tagged nucleotide is presented to the nanopore. Static capture experiments are performed in the presence of Ca2+, which prevents catalysis and elongation of DNA, and allows for the detection of repeated capture of the same type of tagged nucleotide. In this experiment, the tagged nucleotide used was dTnP-tag.

An exemplary polymerase variant Pol6 (S366A+N535L+I652Q) coupled to an alpha hemolysin nanopore on the biochip, and was complexed with template DNA.

The static capture of tagged thymidine nucleotide (Tag is T30 (SEQ ID NO: 9)) by the Pol6 (S366A+N535L+I652Q)-DNA complex was recorded at 100 mV in the presence of 20 mM Hepes7.5, 300 mM NaCl, 3 mM CaCl2 and 5 mM TCEP above and below the bilayer.

Figure 7:
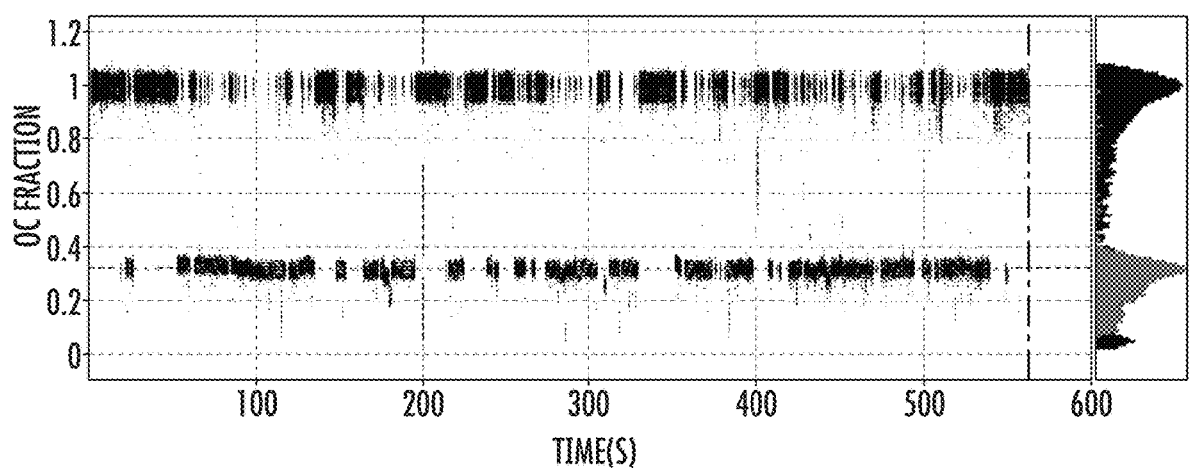
FIG. 7 is a trace of a static capture of tagged thymine nucleotide at 100 mV by Pol6 (S366A+N535L+I652Q)-DNA complex coupled to alpha-hemolysin nanopore in 20 mM Hepes7.5, 300 mM NaCl, 3 mM CaCl2 and 5 mM TCEP above and below the bilayer. The vertical axis is % open channel current (normalized) and horizontal axis is time in seconds. Reference is made to Example 8.
Figure 8:
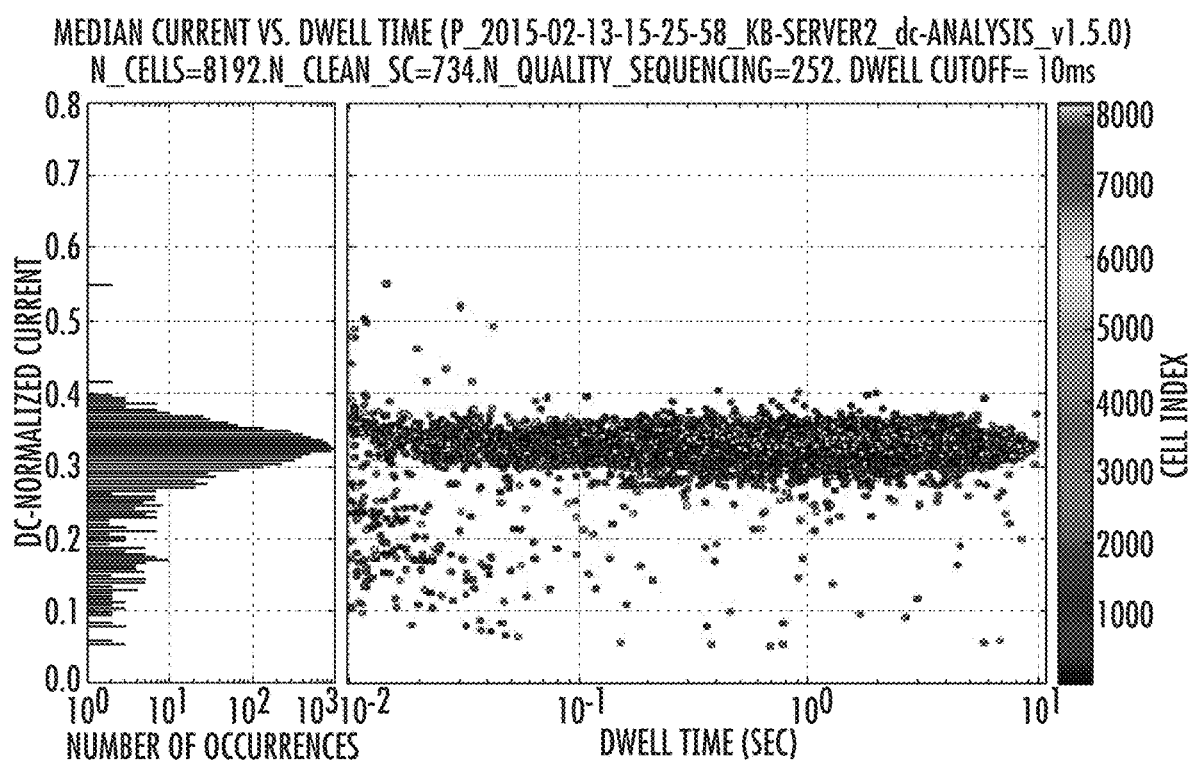
FIG. 8 is graph of Dwell time vs current plot for a static capture experiment at 100 mV with Pol6 (S366A+N535L+ I652Q)-DNA complex coupled to alpha-hemolysin nanopore in 20 mM Hepes pH 7.5, 300 mM NaCl, 3 mM CaCl2 and 5 mM TCEP above and below the bilayer. The average dwell time of each capture of dTNP-tagged nucleotide is 1.2 seconds. Reference is made to Example 8.

The results are shown in FIGS. 7 and 8. The traces in FIG. 7 show electrolytic current measured at 100 mV through the pore as a function of time. The open pore current at this voltage was about 1 nA (uppermost trace); and the blocked pore current at the same voltage was about 0.33 nA (middle trace). The open channel current was normalized to 1 according to the system software, and the blocked channel current was decreased by the dTnP-T30 (SEQ ID NO: 9) to 33% of the open channel current. The current blockades shown in this trace are associated with the binding of thymidine polyphosphate by the variant Pol6-DNA complex, occurring in proximity to the nanopore. The corresponding uppermost histogram in FIG. 7 (right) shows the frequency of current blockades observed at 100 mV with a change in current normalized to the open pore current in the same pore; and the histogram (right) corresponding to the middle trace, shows the frequency of current blockades observed at 100 mV with a change in current normalized to the blocked pore current in the same pore.

FIG. 8 shows Dwell time for the static capture of tagged thymidine shown in FIG. 7. FIG. 8 (left) shows a histogram of the number of occurrences that tagged dTNP was bound by variant Pol6 as a function of the current as normalized to open channel current. The average dwell time of each capture of dTNP-tagged nucleotide was determined to be 1.2 seconds. The background capture (i.e., non-polymerase mediated) of the tag in the pore has a dwell time in the range of a few milliseconds (data not shown). A goal in the enzyme evolution was to improve the dissociation rate of the tagged polyphosphate nucleotide, so you can see dwell times long enough to record a polymerase mediated capture that is well distinguished from background. As shown in FIG. 8, the average dwell time of 1.2 sec is well above the background. The Cell index is a color-based scheme for the approximately 8000 cells present on the chip used in this experiment.

The data show that the exemplary variant polymerase, Pol6 (S366A+N535L+I652Q) is capable of binding tagged nucleotides and to allow for detection in the change in current through the nanopore to which the polymerase is attached.

The results provide evidence that variant polymerases attached to nanopores on a biochip can bind tagged nucleotides with high fidelity, and present the tagged nucleotides to the nanopores for dwell times that provide sufficient time for the detection of nucleotide incorporation, and possibly for decreasing the probability of sequencing errors, e.g., insertions, deletions, etc., during nanopore sequencing.

Example 9

Rolling Circle Amplification Assay

This example describes the amplification of a polynucleotide template in a rolling circle-based assay.

The template used was an in house template HFcirc10. It's a simple circular template ~150 bp long.

The assay was run in a total reaction volume of 40 μl (28 μl of Reagent A+2 μl of 2 μM Polymerase+10 μl of Reagent B).

Reagent A:

| | |
|---|---|
| Kglu | 75 mM |
| HEPES 7.5 | 25 mM |
| EDTA | 0.2 mM |
| Triton X-100 | 0.05 % |
| TCEP | 5 mM |
| BSA | 25 μGg/ml |
| Primed Circular template | 100 nM |
| dNTPs/dN6Ps/Tags | 25 μM |

Reagent B:

| | |
|---|---|
| HEPES 7.5 | 25 mM |
| Kglu | Varied mM |
| Triton X-100 | 0.05 % |
| TCEP | 5 mM |
| BSA | 25 μg/ml |
| MgCl2 | 40 mM |

Two μl of 2 μM polymerase were added to 28 μl Reagent A to give 1:1 molar ratio of DNA to polymerase (100 nM each) in the final 40 μl assay mix. The Reagent A/polymerase mix was incubated for 10 min in this 75 mM salt condition to allow polymerase to bind DNA.

Next, 10 μl of Reagent B were added to the to the Reagent A/polymerase mixture to start the reaction.

At pre-determined time points, 10 μl samples were removed from the reaction and added to 10 μl formamide with 50 mM EDTA to quench the reaction. Samples were taken at time points 0 min, 10 min, 30 min and 40 minutes.

The formamide samples were heated to 94° C. for approximately 3 min to denature proteins and secondary structures of DNA. The samples were not allowed to cool down to 4° C. Add 2 μl of 100×SYBR GREEN or GOLD dye.

15 μl of each sample was run on a 1.2% Agarose gel for 1 hour 15 minutes at 100V.

An image of the gel was acquired using the blue tray for the Biorad GEL DOC EZ imager.

Figure 11:
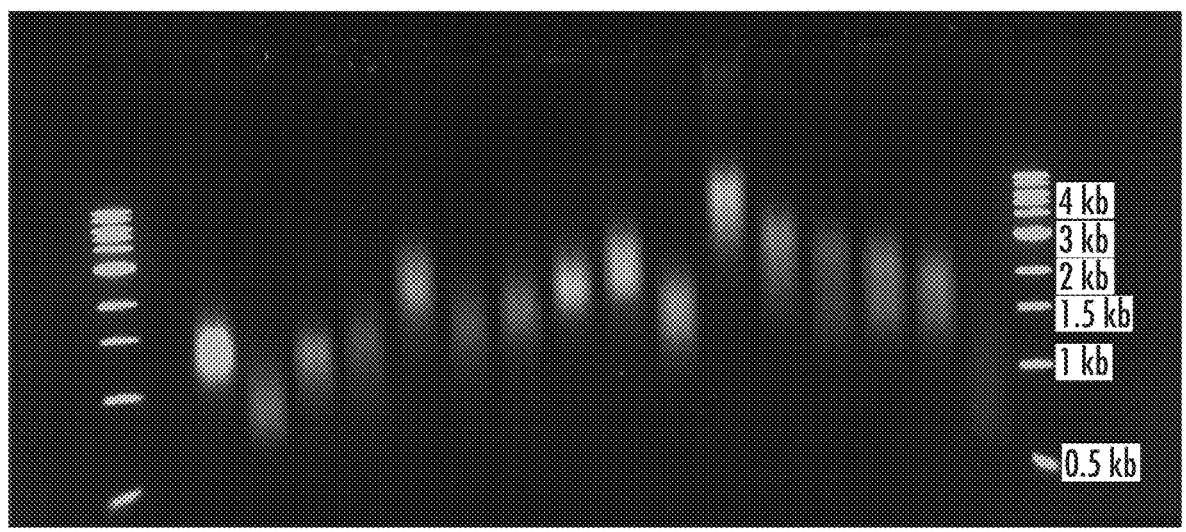
FIG. 11 is a picture of a gel showing the amplification products of a rolling circle assay. The left and right end lanes are molecular ladders. The lane second from the left is the zero time point. All other lanes are the 40-minute time point for the various polymerase hits. Reference is made to Example 9.

FIG. 11 shows the 40 minute time point results of the assay. A molecular ladder is shown in lanes 1 and 19, numbering left to right. Lane 2 has a sample from t=0; no product is visible. Each of lanes 3-18 is a different variant pol6 polymerase.

All variants shown are able to do strand displacement and generate long kilo base DNA products with all hexaphosphate nucleotides.

Example 10

Sequencing Template DNA Using Tagged Nucleotides

This example demonstrates that the variant polymerase is functional in a sequencing by synthesis method on a biochip.

Figure 12:
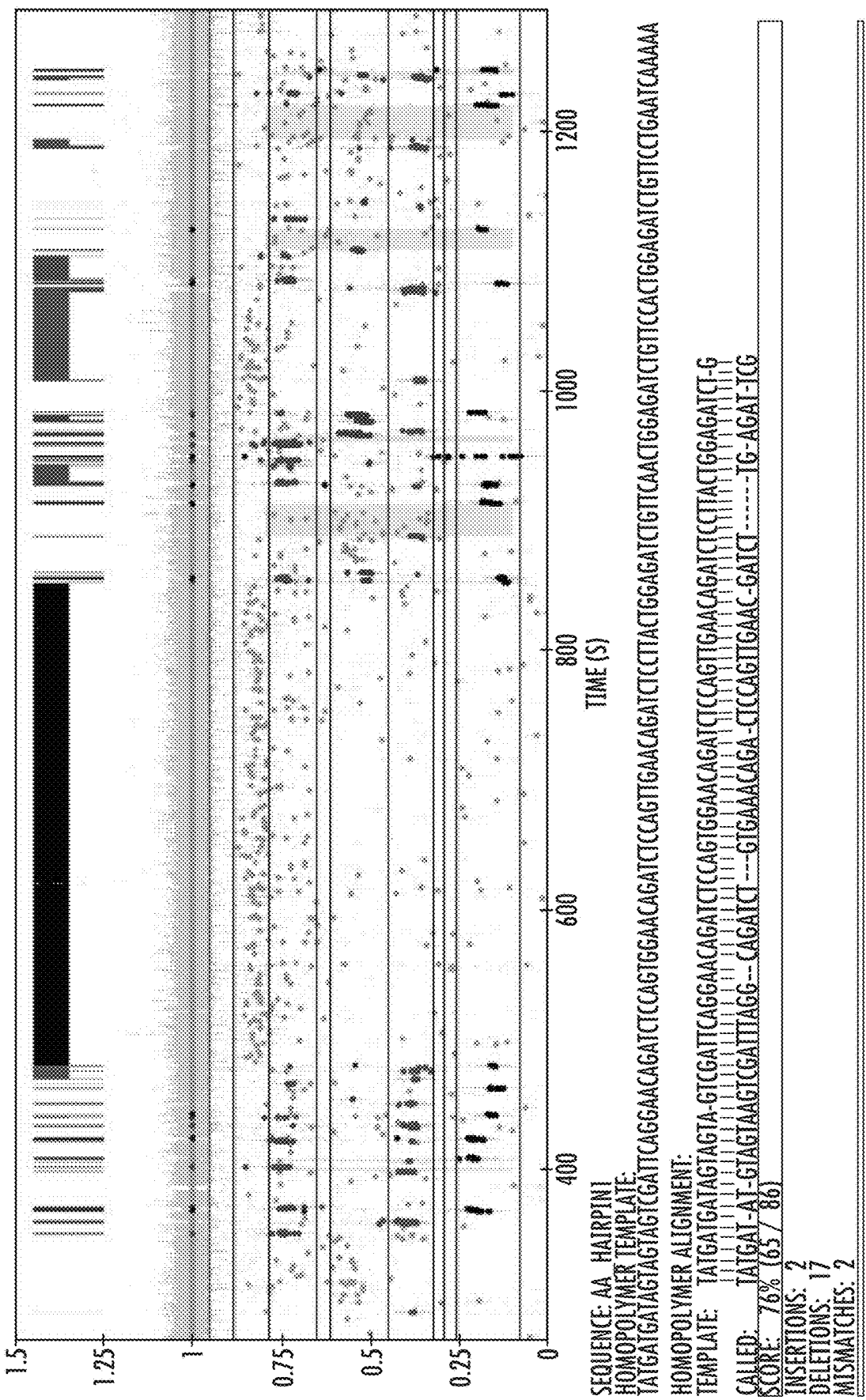
FIG. 12 is a sequencing trace showing the changes in current that provides a record of the tagged nucleotides as they are incorporated into the growing DNA strand. Also shown is the template DNA sequence and the called sequence of the nascent strand demonstrating >70% accuracy (SEQ ID NOS 6-8, respectively, in order of appearance). Reference is made to Example 10.

AC sequencing of a heteropolymer template using Pol6-26i-D44A polymerase at 20 mM Hepes, pH 8, 500 mM Potassium Glutamate and 3 mM MgCl2 at room temperature. A nanopore with attached polymerase was embedded in the lipid bilayer as described herein. Primed DNA was added and allowed to complex with the polymerase. Four different tagged nucleotides were added at a concentration of 25 μM. The sequencing by synthesis may proceed as described in WO 2014/074727 entitled "Nucleic Acid Sequencing Using Tags." The trace in FIG. 12 shows a sequencing accuracy of 76% for a heteropolymer template and 96 bp read length.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

SEQUENCE LISTING FREE TEXT
Wild-type Pol6 (DNA polymerase [*Clostridium* phage phiCPV4];
GenBank: AFH27113.1)

SEQ ID NO: 1

```
  1 mdkhtqyvke hsfnydeykk anfdkiecli fdtesctnye ndntgarvyg wglgvtrnhn
 61 miygqnlnqf wevcqnifnd wyhdnkhtik itktkkgfpk rkyikfpiav hnlgwdvefl
121 kyslvengfn ydkgllktvf skgapyqtvt dveepktfhi vqnnnivygc nvymdkffev
181 enkdgsttei glcldffdsy kiitcaesqf hnyvhdvdpm fykmgeeydy dtwrspthkq
241 ttlelryqyn diymlrevie qfyidglcgg elpltgmrta ssiafnvlkk mtfgeektee
301 gyinyfeldk ktkfeflrkr iemesytggy thanhkavgk tinkigcsld inssypsqma
361 ykvfpygkpv rktwgrkpkt eknevyliev gfdfvepkhe eyaldifkig avnskalspi
421 tgaysgqeyf ctnikdgkai pvykelkdtk lttnynvvlt sveyefwikh fnfgvfkkde
481 ydcfevdnle ftglkigsil yykaekgkfk pyvdhftkmk venkklgnkp ltnqakliln
541 gaygkfgtkq nkeekdlimd knglltftgs vteyegkefy rpyasfvtay grlqlwnaii
601 yavgvenfly cdtdsiycnr evnsliedmn aigetidkti lgkwdvehvf dkfkvlgqkk
661 ymyhdckedk tdlkccglps darkiiigqg fdefylgknv egkkqrkkvi ggcllldtlf
721 tikkimf
```

Pol6 (with His tag)

SEQ ID NO: 2

| | | | | |
|---|---|---|---|---|
| MHHHHHHHS | GGSDKHTQYV | KEHSFNYDEY | KKANFDKIEC | LIFDTESCTN | 50 |
| YENDNTGARV | YGWGLGVTRN | HNMIYGQNLN | QFWEVCQNIF | NDWYHDNKHT | 100 |
| IKITKTKKGF | PKRKYIKFPI | AVHNLGWDVE | FLKYSLVENG | FNYDKGLLKT | 150 |
| VFSKGAPYQT | VTDVEEPKTF | HIVQNNNIVY | GCNVYMDKFF | EVENKDGSTT | 200 |
| EIGLCLDFFD | SYKIITCAES | QFHNYVHDVD | PMFYKMGEEY | DYDTWRSPTH | 250 |
| KQTTLELRYQ | YNDIYMLREV | IEQFYIDGLC | GGELPLTGMR | TASSIAFNVL | 300 |
| KKMTFGEEKT | EEGYINYFEL | DKKTKFEFLR | KRIEMESYTG | GYTHANHKAV | 350 |
| GKTINKIGCS | LDINSSYPSQ | MAYKVFPYGK | PVRKTWGRKP | KTEKNEVYLI | 400 |
| EVGFDFVEPK | HEEYALDIFK | IGAVNSKALS | PITGAVSGQE | YFCTNIKDGK | 450 |
| AIPVYKELKD | TKLTTNYNVV | LTSVEYEFWI | KHFNFGVFKK | DEYDCFEVDN | 500 |
| LEFTGLKIGS | ILYYKAEKGK | FKPYVDHFTK | MKVENKKLGN | KPLTNQAKLI | 550 |
| LNGAYGKFGT | KQNKEEKDLI | MDKNGLLTFT | GSVTEYEGKE | FYRPYASFVT | 600 |
| AYGRLQLWNA | IIYAVGVENF | LYCDTDSIYC | NREVNSLIED | MNAIGETIDK | 650 |
| TILGKWDVEH | VFDKFKVLGQ | KKYMYHDCKE | DKTDLKCCGL | PSDARKIIIG | 700 |
| QGFDEFYLGK | NVEGKKQRKK | VIGGCLLLDT | LFTIKKIMF* | | 739 |

Pol6 with His-tag (DNA sequence)

SEQ ID NO: 3

| | | | | |
|---|---|---|---|---|
| ATGCATCACC | ATCATCATCA | CCACCACAGC | GGCGGTTCCG | ACAAACACAC | 50 |
| GCAGTACGTC | AAAGAGCATA | GCTTCAATTA | TGACGAGTAT | AAGAAAGCGA | 100 |
| ATTTCGACAA | GATCGAGTGC | CTGATCTTTG | ACACCGAGAG | CTGCACGAAT | 150 |
| TATGAGAACG | ATAATACCGG | TGCACGTGTT | TACGGTTGGG | GTCTTGGCGT | 200 |
| CACCCGCAAC | CACAATATGA | TCTACGGCCA | AAATCTGAAT | CAGTTTTGGG | 250 |
| AAGTATGCCA | GAACATTTTC | AATGATTGGT | ATCACGACAA | CAAACATACC | 300 |
| ATTAAGATTA | CCAAGACCAA | GAAAGGCTTC | CCGAAACGTA | AGTACATTAA | 350 |
| GTTTCCGATT | GCAGTTCACA | ATTTGGGCTG | GGATGTTGAA | TTCCTGAAGT | 400 |
| ATAGCCTGGT | GGAGAATGGT | TTCAATTACG | ACAAGGGTCT | GCTGAAAACT | 450 |

```
GTTTTTAGCA AGGGTGCGCC GTACCAAACC GTGACCGATG TTGAGGAACC      500

GAAAACGTTC CATATCGTCC AGAATAACAA CATCGTTTAT GGTTGTAACG      550

TGTATATGGA CAAATTCTTT GAGGTCGAGA ACAAAGACGG CTCTACCACC      600

GAGATTGGCC TGTGCTTGGA TTTCTTCGAT AGCTATAAGA TCATCACGTG      650

TGCTGAGAGC CAGTTCCACA ATTACGTTCA TGATGTGGAT CCAATGTTCT      700

ACAAAATGGG TGAAGAGTAT GATTACGATA CTTGGCGTAG CCCGACGCAC      750

AAGCAGACCA CCCTGGAGCT GCGCTACCAA TACAATGATA TCTATATGCT      800

GCGTGAAGTC ATCGAACAGT TTTACATTGA CGGTTTATGT GGCGGCGAGC      850

TGCCGCTGAC CGGCATGCGC ACCGCTTCCA GCATTGCGTT CAACGTGCTG      900

AAAAAGATGA CCTTTGGTGA GGAAAAGACG GAAGAGGGCT ACATCAACTA      950

TTTTGAATTG GACAAGAAAA CCAAATTCGA GTTTCTGCGT AAGCGCATTG     1000

AAATGGAATC GTACACCGGT GGCTATACGC ACGCAAATCA CAAAGCCGTT     1050

GGTAAGACTA TTAACAAGAT CGGTTGCTCT TTGGACATTA ACAGCTCATA     1100

CCCTTCGCAG ATGGCGTACA AGGTCTTTCC GTATGGCAAA CCGGTTCGTA     1150

AGACCTGGGG TCGTAAACCA AAGACCGAGA AGAACGAAGT TTATCTGATT     1200

GAAGTTGGCT TTGACTTCGT GGAGCCGAAA CACGAAGAAT ACGCGCTGGA     1250

TATCTTTAAG ATTGGTGCGG TGAACTCTAA AGCGCTGAGC CCGATCACCG     1300

GCGCTGTCAG CGGTCAAGAG TATTTCTGTA CGAACATTAA AGACGGCAAA     1350

GCAATCCCGG TTTACAAAGA ACTGAAGGAC ACCAAATTGA CCACTAACTA     1400

CAATGTCGTG CTGACCAGCG TGGAGTACGA GTTCTGGATC AAACACTTCA     1450

ATTTTGGTGT GTTTAAGAAA GACGAGTACG ACTGTTTCGA AGTTGACAAT     1500

CTGGAGTTTA CGGGTCTGAA GATTGGTTCC ATTCTGTACT ACAAGGCAGA     1550

GAAAGGCAAG TTTAAACCTT ACGTGGATCA CTTCACGAAA ATGAAAGTGG     1600

AGAACAAGAA ACTGGGTAAT AAGCCGCTGA CGAATCAGGC AAAGCTGATT     1650

CTGAACGGTG CGTACGGCAA ATTCGGCACC AAACAAAACA AGAAGAGAA      1700

AGATTTGATC ATGGATAAGA ACGGTTTGCT GACCTTCACG GGTAGCGTCA     1750

CGGAATACGA GGGTAAAGAA TTCTATCGTC CGTATGCGAG CTTCGTTACT     1800

GCCTATGGTC GCCTGCAACT GTGGAACGCG ATTATCTACG CGGTTGGTGT     1850

GGAGAATTTT CTGTACTGCG ACACCGACAG CATCTATTGT AACCGTGAAG     1900

TTAACAGCCT CATTGAGGAT ATGAACGCCA TTGGTGAAAC CATCGATAAA     1950

ACGATTCTGG GTAAATGGGA CGTGGAGCAT GTCTTTGATA AGTTTAAGGT     2000

CCTGGGCCAG AAGAAGTACA TGTATCATGA TTGCAAAGAA GATAAAACGG     2050

ACCTGAAGTG TTGCGGTCTG CCGAGCGATG CCCGTAAGAT TATCATTGGT     2100

CAAGGTTTCG ACGAGTTTTA TCTGGGCAAA AATGTCGAAG GTAAGAAGCA     2150

ACGCAAAAAA GTGATCGGCG GTTGCCTGCT GCTGGACACC CTGTTTACGA     2200

TCAAGAAAAT CATGTTCTAA                                      2220
```

CITATION LIST

Patent Literature

[1] PCT/US2005/009702 (published as WO2006/028508 on 16 Mar. 2006; President and Fellows of Harvard College; entitled METHODS AND APPARATUS FOR CHARACTERIZING POLYNUCLEOTIDES).

[2] PCT/US2011/065640 (published as WO2012/083249 on 21 Jun. 2012; Columbia University; entitled DNA SEQUENCING BY SYNTHESIS USING MODIFIED NUCLEOTIDES AND NANOPORE DETECTION).

[3] PCT/US2013/068967 (published as WO2014/074727 on 15 May 2014; Genia Technologies; entitled NUCLEIC ACID SEQUENCING USING TAGS).
[4] PCT/US2013/046012 (Genia Technologies, Inc., entitled CHIP SET-UP AND HIGH-ACCURACY NUCLEIC ACID SEQUENCING, published 19 Dec. 2013 as WO2013/188841).
[5] US 2013/0053544 (Isis Innovation Limited) entitled Peptide Tag Systems That Spontaneously Form an Irreversible Link to Protein Partners via Isopeptide Bonds, published 28 Feb. 2013.

Non-Patent Literature

[1] Altschul, S. F., et al., J. Mol. Biol. (1990) 215:403-410.
[2] Altschul, S. F., et al., Nucleic Acids Res. 25:3389-3402, 1997.
[3] Ausubel, Frederick et al., (1992) Short Protocols in Molecular Biology, Current Protocols in Molecular Biology, 2nd ed., Greene Publishing Associates & John Wiley & Sons. New York, N.Y.
[4] Gardner et al., Nucleic Acids Res. (2012) pages 1-12 (doi: 10.1093/nar/gks330; First published online: May 8, 2012).
[5] Hale & Marham, THE HARPER COLLINS DICTIONARY OF BIOLOGY, Harper Perennial, N.Y. (1991).
[6] Johnson, et al., Biochim Biophys Acta. 2010 May; 1804(5):1041-1048.
[7] Kong et al. (1993) *J. Biol. Chem.* 268(3):1965-1975.
[8] Lawyer et al. (1989) *J. Biol. Chem.* 264:6427-647.
[9] Li et al, Structural Analysis and Optimization of the Covalent Association between SpyCatcher and a Peptide Tag; *J Mol Biol.* (2014 Jan. 23) 426(2):309-17.
[10] Sambrook et al., (1989) Molecular Cloning: A Laboratory Manual ($2^{nd}$ ed., Cold Spring Harbor Laboratory Press, NY).
[11] Sambrook et al. (2001) Molecular Cloning: A Laboratory Manual (3rd ed., Cold Spring Harbor Laboratory Press, NY) at 9.63-9.75 (describing end-labeling of nucleic acids).
[12] Singleton, et al., DICTIONARY OF MICROBIOLOGY AND MOLECULAR BIOLOGY, 2D ED., John Wiley and Sons, New York (1994).
[13] Watson, J. D. et al., In: Molecular Biology of the Gene, 4th Ed., W. A. Benjamin, Inc., Menlo Park, Calif. (1987)).
[14] Zakari and Howarth, (2010) Spontaneous Intermolecular Amide Bond Formation between Side Chains for Irreversible Peptide Targeting, J. Am. Chem. Soc., 132 (13):4526-4527.
[15] Zakari, B. et al., (2012) Peptide tag forming a rapid covalent bond to a protein, through engineering a bacterial adhesion, PNAS 109 (12):E690-E697.

What is claimed is:

1. A modified deoxyribonucleic acid (DNA) polymerase comprising an amino acid sequence having at least 95% sequence identity to SEQ ID NO: 2, which amino acid sequence includes an amino acid substitution selected from the group consisting of Y225M, H227E/F/Y, S360E/Y, L361F, I363A/R/M/W, Y367F, H527Y/T/M, M531G, N535R/W/Q, P542G, N545Q/W, L549K, N552T, G553E/Q/K/R/M, G603A/L, C623F, D624K, I628L/M, Y629K, T647Y, I648L, I652A/L/E/K/M, K655Q/M/A, and D657E.

2. The modified DNA polymerase of claim 1, wherein modified DNA polymerase is capable of incorporating a tagged deoxyribonucleotide tetraphosphate, a tagged deoxyribonucleotide pentaphosphate, a tagged deoxyribonucleotide hexaphosphate, a tagged deoxyribonucleotide heptaphosphate, and/or a tagged deoxyribonucleotide octophosphate into a growing DNA strand.

3. The modified DNA polymerase of claim 2, wherein the tag is attached to a terminal phosphate of the polyphosphate deoxyribonucleotide.

4. The modified DNA polymerase of claim 1, wherein the modified DNA polymerase has an altered characteristic as compared to a DNA polymerase consisting of SEQ ID NO: 2.

5. The modified DNA polymerase of claim 1, wherein the amino acid sequence further includes T529M, S366A, A547F, N545L, Y225L, and D657R substitutions.

* * * * *